United States Patent
Golstein et al.

(12)

(10) Patent No.: US 6,274,711 B1
(45) Date of Patent: *Aug. 14, 2001

(54) PURIFIED MAMMALIAN CTLA-8 ANTIGENS AND RELATED REAGENTS

(75) Inventors: Pierre Golstein; Eric Rouvier, both of Marseille; Francois Fossiez, Craponne; Serge J. E. Lebecque, Chazay d'Azerques; Odile Djossou, Francheville; Jacques Banchereau, Ecully, all of (FR)

(73) Assignees: INSERM, Institut National de la Sante et de la Recherche Medicale, Paris (FR); Schering Corporation, Kenilworth, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/432,994

(22) Filed: May 2, 1995

Related U.S. Application Data

(63) Continuation-in-part of application No. 08/250,846, filed on May 27, 1994, now abandoned, which is a continuation-in-part of application No. 08/177,747, filed on Jan. 5, 1994, now abandoned, which is a continuation-in-part of application No. 08/077,203, filed on Jun. 14, 1993, now abandoned.

(51) Int. Cl.$^7$ .................................................. C07K 16/00
(52) U.S. Cl. ..................... 530/389.2; 530/387.9; 530/388.23; 530/391.3; 435/975
(58) Field of Search ........................ 530/388.23, 387.9, 530/389.2, 391.3; 435/975

(56) References Cited

PUBLICATIONS

Randall et al. J. Gen. Virol., vol. 66: 2199–2213, Jun. 1985.*
Nicholas et al. Virology, vol. 179:189–200, Aug. 1990.*
Johnstone et al. Immuno Chemistry in Practice. 1988 Second edition. Blackwell Scientific Oxford.*
Jens–Christian Albrecht, et al., "Primary Structure of the Herpesvirus Saimiri Genome," *Journal of Virology*, vol. 66, No. 8, pp. 5047–5058, Aug. 1992.
Jens–Christian Albrecht, et al., "Structural Organization of the Conserved Gene Block of *Herpesvirus saimiri* Coding for DNA Polymerases, Glycoprotein B, and Major DNA Binding Protein," *Virology*, vol. 174, pp. 533–542, 1990.
D. Caput, et al., "Identification of a common nucleotide sequence in the 3'–untranslated region of mRNA molecules specifying inflammatory mediators," *Proc. Nat'l. Acad. Sci.*, vol. 83, pp. 1670–1674, Mar. 1986.

Marilyn Kozak, "An analysis of Vertebrate mRNA sequences: Intimations of Translational Control," *The Journal of Cell Biology*, vol. 115, No. 4, pp. 887–903, Nov. 1991.
Marilyn Kozak, "Structural Features in Eukaryotic mRNAs that Modulate the Initiation of Translation," *J. Biol. Chem.*, vol. 266, No. 30, pp. 19867–19870, Oct. 1991.
John Nicholas, et al., "Gene Expression in Cells Infected with Gammaherpes–virus Saimiri: Properties of Transcripts from Two Immediate–Early Genes," *Virology*, vol. 179, pp. 189–200, 1990.
John Nicholas, et al., Gen Bank Accession No. M60286, pp. 1–3, Mar. 1991.
Marc Piechaczyk, et al., "Role of RNA Structures in c–myc and c–fos Gene Regulations," *Gene*, vol. 72, pp. 287–295, 1988.
Eric Rouvier, et al., "CTLA–8, Cloned from an Activated T Cell, Bearing AU–Rich Messenger RNA Instability Sequences, and Homologous to a Herpesvirus Saimiri Gene," *The Journal of Immunology*, vol. 150, No. 12, pp. 5445–5456, Jun. 1993.
Eric Rouvier, et al., Gen Bank Accession No. L13839, pp. 1–2, Apr. 1993.
Eric Rouvier, et al., "A Search for Novel Molecules Differentially Expressed in Cytotoxic T Cells, " Abstract and poster presented at the International Congress of Immunology, Budapest, Hungary, abstract and poster panels, Aug. 1992.
Gray Shaw, et al., "A Conserved AU Sequence from the 3'–Ultranslated Region of GM–CSF mRNA Mediates Selective mRNA Degradation," *Cell*, vol. 46, pp. 659–667, Aug. 1986.
Sabine Miller, et al. "Cloning of ATAC, and Activation–Induced, Chemokine–Related Molecule Exclusively Expressed in $CD8_+$ T Lymphocytes," *Eur. J. Immunol.* 25;1744–1748, 1995.
Tetsuya Yoshida, et al. "Molecular Cloning of a Novel C or γ Type Chemokine, SCM–1," *FEBS Letters* 360:155–159, 1995.
A. Neil Barclay et al., "The Leucocyte Antigen Facts Book," 1993, Academic Press Limited, London pp. 290–291.
Hyrun Soon Lillehoj, et al., "Functional and Biochemical Characterizations of Avian T Lymphocyte Antigens Identified by Monoclonal Antibodies," *Eur. J. Immunol.*, 18:2059–2065, 1988.

* cited by examiner

*Primary Examiner*—Patrick Nolan
(74) *Attorney, Agent, or Firm*—Kenneth A. Weber; Edwin P. Ching

(57) ABSTRACT

CTLA-8 antigen from a mammal, reagents related thereto including purified proteins, specific antibodies, and nucleic acids encoding said antigen. Methods of using said reagents and diagnostic kits are also provided.

7 Claims, No Drawings

PURIFIED MAMMALIAN CTLA-8 ANTIGENS AND RELATED REAGENTS

The present application is a continuation-in-part of U.S. Ser. No. 08/250,846, filed May 27, 1994, now abandoned which is a continuation-in-part of then patent application U.S. Ser. No. 08/177,747, filed Jan. 5, 1994, now abandoned which is a continuation-in-part of then patent application U.S. Ser. No. 08/077,203, filed Jun. 14, 1993, now abandoned each of which is incorporated herein by reference. Also incorporated by reference is co-pending PCT/US95/00001, filed Jan. 3, 1995.

FIELD OF THE INVENTION

The present invention relates to compositions related to proteins which function in controlling physiology, development, and differentiation of mammalian cells, e.g., cells of a mammalian immune system. In particular, it provides proteins and mimetics which regulate cellular physiology, development, differentiation, or function of various cell types, including hematopoietic cells.

BACKGROUND OF THE INVENTION

The immune system of vertebrates consists of a number of organs and several different cell types. Two major cell types include the myeloid and lymphoid lineages. Among the lymphoid cell lineage are B cells, which were originally characterized as differentiating in fetal liver or adult bone marrow, and T cells, which were originally characterized as differentiating in the thymus. See, e.g., Paul (ed.) (1993) *Fundamental Immunology* (3d ed.) Raven Press, New York.

In many aspects of the development of an immune response or cellular differentiation, soluble proteins known as cytokines play a critical role in regulating cellular interactions. These cytokines apparently mediate cellular activities in many ways. They have been shown, in many cases, to modulate proliferation, growth, and differentiation of hematopoietic stem cells into the vast number of progenitors composing the lineages responsible for an immune response.

However, the cellular molecules which are expressed by different developmental stages of cells in these maturation pathways are still incompletely identified. Moreover, the roles and mechanisms of action of signaling molecules which induce, sustain, or modulate the various physiological, developmental, or proliferative states of these cells is poorly understood. Clearly, the immune system and its response to various stresses had relevance to medicine, e.g., infectious diseases, cancer related responses and treatment, allergic and transplantation rejection responses. See, e.g., Thorn, et al. *Harrison's Principles of Internal Medicine* McGraw/Hill, New York.

Medical science relies, in large degree, to appropriate recruitment or suppression of the immune system in effecting cures for insufficient or improper physiological responses to environmental factors. However, the lack of understanding of how the immune system is regulated or differentiates has blocked the ability to advantageously modulate the normal defensive mechanisms to biological challenges. Medical conditions characterized by abnormal or inappropriate regulation of the development or physiology of relevant cells thus remain unmanageable. The discovery and characterization of specific cytokines will contribute to the development of therapies for a broad range of degenerative or other conditions which affect the immune system, hematopoietic cells, as well as other cell types. The present invention provides solutions to some of these and many other problems.

SUMMARY OF THE INVENTION

The present invention is based, in part, upon the discovery of a cDNA clone encoding a cytokine-like protein. This protein has been designated CTLA-8. The invention embraces isolated genes encoding the proteins of the invention, variants of the encoded protein, e.g., mutations (muteins) of the natural sequence, species and allelic variants, fusion proteins, chemical mimetics, antibodies, and other structural or functional analogs. Various uses of these different nucleic acid or protein compositions are also provided.

The present invention embraces isolated genes encoding the proteins of the invention, variants of the encoded protein, e.g., mutations (muteins) of the natural sequence, species and allelic variants, fusion proteins, chemical mimetics, antibodies, and other structural or functional analogs. Various uses of these different nucleic acid or protein compositions are also provided.

The present invention provides a nucleic acid with at least 95% identity to one encoding a mammalian CTLA-8 protein or fragment thereof. The encoding nucleic acid can comprise a sequence of SEQ ID NO: 1, 3, 5, 7, or 9.

The present invention also provides a substantially pure mammalian CTLA-8 protein or peptide thereof. The protein or peptide can comprise at least one polypeptide segment of SEQ ID NO: 2, 4, 6, 8, or 10; exhibit a post-translational modification pattern distinct from a natural mammalian CTLA-8 protein; or induce a cell to secrete an inflammatory mediator, e.g., IL-6, IL-8, and/or PGE2. A further embodiment is a composition comprising such a protein and a pharmaceutically acceptable carrier.

The invention includes an antibody which specifically binds to a primate CTLA-8 protein or peptide thereof; the antibody is raised against a protein sequence of SEQ ID NO: 2, 4, 6, 8 or 10; the antibody is a monoclonal antibody; the antibody blocks the CTLA-8 induced secretion of an inflammatory mediator, e.g., IL-6, IL-8, and/or PGE2; or the antibody is labeled.

The invention also embraces a kit comprising a substantially pure nucleic acid at least 95% identical to one encoding a mammalian CTLA-8 protein or peptide; a substantially pure mammalian CTLA-8 protein or fragment, e.g., as a positive control; or an antibody or receptor which specifically binds a mammalian CTLA-8 protein.

The availability of these reagents also provides methods of modulating physiology or development of a cell comprising contacting said cell with an agonist or antagonist of a CTLA-8 protein. The method of modulation encompasses regulating CTLA-8 induced secretion of an inflammatory mediator, e.g., IL-6, IL-8, and/or PGE2, by contacting the cell or tissue with an antibody which specifically binds mammalian CTLA-8 or a substantially pure mammalian CTLA-8 protein. Preferably, the cell can be a synovial cell, epithelial cell, endothelial cell, fibroblast cell, or a carcinoma cell.

DETAILED DESCRIPTION OF THE PREFERRED EMBODIMENTS

Outline

I. General

II. Nucleic Acids

A. natural isolates; methods

B. synthetic genes

C. methods to isolate

III. Purified CTLA-8 protein
  A. physical properties
  B. biological properties
IV. Making CTLA-8 protein; Mimetics
  A. recombinant methods
  B. synthetic methods
  C. natural purification
V. Physical Variants
  A. sequence variants, fragments
  B. post-translational variants
    1. glycosylation
    2. others
VI. Functional Variants
  A. analogs; fragments
    1. agonists
    2. antagonists
  B. mimetics
    1. protein
    2. chemicals
  C. species variants
VII. Antibodies
  A. polyclonal
  B. monoclonal
  C. fragments, binding compositions
VIII. Uses
  A. diagnostic
  B. therapeutic
IX. Kits
  A. nucleic acid reagents
  B. protein reagents
  C. antibody reagents
I. General The present invention provides DNA sequence encoding various mammalian proteins which exhibit properties characteristic of functionally significant T cell expressed molecules. The cDNA sequence exhibits various features which are characteristic of mRNAs encoding cytokines, growth factors, and oncogenes. A murine gene originally thought to be from a mouse, but now recognized as rat as described herein contains an open reading frame encoding a putative 150 amino acid protein. This protein is 57% homologous to a putative protein encoded by a viral genome, the herpesvirus Saimiri ORF13. The message was isolated using a subtraction hybridization method applied to T cells.

These proteins are designated CTLA-8 proteins. The natural proteins should be capable of mediating various physiological responses which would lead to biological or physiological responses in target cells. Initial studies had localized the message encoding this protein to various cell lines of hematopoietic cells. Genes encoding the antigen have been mapped to mouse chromosome 1A and human chromosome 2q31. Murine CTLA-8 was originally cloned by Rouvier, et al. (1993) *J. Immunol.* 150:5445–5456. Similar sequences for proteins in other mammalian species should also be available.

Purified CTLA-8, when cultured with synoviocytes, is able to induce the secretion of IL-6 from these cells. This induction is reversed upon the addition of a neutralizing antibody raised against human CTLA-8-8. Endothelial, epithelial, fibroblast and carcinoma cells also exhibit responses to treatment with CTLA-8. This data suggests that CTLA-8 may be implicated in inflammatory fibrosis, e.g., psoriasis, sclerodermia, lung fibrosis, or cirrhosis. CTLA-8 may also cause proliferation of carcinomas or other cancer cells inasmuch as IL-6 often acts as a growth factor for such cells.

The descriptions below are directed, for exemplary purposes, to a murine or human CTLA-8 protein, but are likewise applicable to related embodiments from other species.

II. Nucleic Acids

Table 1 discloses the nucleotide and amino acid sequences of a murine CTLA-8 protein. The described nucleotide sequences and the related reagents are useful in constructing a DNA clone useful for expressing CTLA-8 protein, or, e.g., isolating a homologous gene from another natural source. Typically, the sequences will be useful in isolating other genes, e.g., allelic variants, from mouse, and similar procedures will be applied to isolate genes from other species, e.g., warm blooded animals, such as birds and mammals. Cross hybridization will allow isolation of genes from other species. A number of different approaches should be available to successfully isolate a suitable nucleic acid clone from other sources.

TABLE 1

Nucleotide sequence, SEQ ID NO.1, encoding a murine CTLA-8 protein and predicted amino acid sequence. Also can use complementary nucleic acid sequences for many purposes. Submitted to GenBank/EMBL under accession number L13839.

```
  1 GAATTCCATC CATGTGCCTG ATGCTGTTGC TGCTACTGAA CCTGGAGGCT ACAGTGAAGG

61 CAGCGGTACT CATCCCTCAA AGTTCAGTGT GTCCAAACGC CGAGGCCAAT AACTTTCTCC

121 AGAACGTGAA GGTCAACCTG AAAGTCATCA ACTCCCTTAG CTCAAAAGCG AGCTCCAGAA

181 GGCCCTCAGA CTACCTCAAC CGTTCCACTT CACCCTGGAC TCTGAGCCGC AATGAGGACC

241 CTGATAGATA TCCTTCTGTG ATCTGGGAGG CACAGTGCCG CCACCAGCGC TGTGTCAACG

301 CTGAGGGGAA GTTGGACCAC CACATGAATT CTGTTCTCAT CCAGCAAGAG ATCCTGGTCC

361 TGAAGAGGGA GCCTGAGAAG TGCCCCTTCA CTTTCCGGGT GGAGAAGATG CTGGTGGGCG

421 TGGGCTGCAC CTGCGTTTCC TCTATTGTCC GCCATGCGTC CTAAACAGAG ACCTGAGGCT

481 AGCCCCTAAG AAACCCCTGC GTTTCTCTGC AAACTTCCTT GTCTTTTTAA AACAGTTCAC
```

TABLE 1-continued

Nucleotide sequence, SEQ ID NO.1, encoding a murine CTLA-8 protein and predicted amino acid sequence. Also can use complementary nucleic acid sequences for many purposes. Submitted to GenBank/EMBL under accession number L13839.

```
 541 AGTTGAATCT CAGCAAGTGA TATGGATTTA AAGGCGGGGT TAGAATTGTC TGCCTTCCAC

601 CCTGAAAAGA AGGCGCAGAG GGGATATAAA TTGCTTCTTG TTTTTCTGTG GGCTTTAAAT

661 TATTTATGTA TTTACTCTAT CCCGAGATAA CTTTGAGGCA TAAGTTATTT TAATGAATTA

721 TCTACATTAT TATTATGTTT CTTAATGCAG AAGACAAAAT TCAAGACTAA GAAATTTTAT

781 TATTTAAAAG GTAAAACCTA TATTTATATG AGCTATTTAT GGGTCTATTT ATTTTTCTTC

841 AGTGCTAAGA TCATGATTAT CAGATCTACC TAAGGAAGTC CTAAATAATA TTAAATATTA

901 ATTGAAATTT CAGTTTTACT ATTTGCTTAT TTAAGGTTCC CTCCTCTGAA TGGTGTGAAA

961 TCAAACCTCG TTTTATGTTT TTAAATTATT GAGGCTTCGA AAAATTGGGC AATTTAGCTT

1021 CCTACTGTGT GTTTAAAAAC CTTGTAACAA TATCACTATA ATAAATTTTT GGAAGAAAAT
``` predicted amino acid sequence, SEQ ID NO.2 (150 amino acids).
Mature polypeptide
probably starts at about amino acid 13(Ala).

```
MCLML LLLLN LEATV KAAVL IPQSS VCPNA EANNF LQNVK VNLKV INSLS
SKASS RRPSD YLNRS TSPWT LSRNE DPDRY PSVIW EAQCR HQRCV NAEGK
LDHHM NSLVI QQEIL VLKRE PEKCP FTFRV EKMLV GVGCT CVSSI VRHAS
```

The purified protein or defined peptides are useful for generating antibodies by standard methods, as described above. Synthetic peptides or purified protein can be presented to an immune system to generate a specific binding composition, e.g., monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press.

For example, the specific binding composition could be used for screening of an expression library made from a cell line which expresses a CTLA-8 protein. The screening can be standard staining of surface expressed protein, or by panning. Screening of intracellular expression can also be performed by various staining or immunofluorescence procedures. The binding compositions could be used to affinity purify or sort out cells expressing the protein.

This invention contemplates use of isolated DNA or fragments to encode a biologically active corresponding CTLA-8 protein or polypeptide. In addition, this invention covers isolated or recombinant DNA which encodes a biologically active protein or polypeptide and which is capable of hybridizing under appropriate conditions with the DNA sequences described herein. Said biologically active protein or polypeptide can be an intact antigen, or fragment, and have an amino acid sequence as disclosed in Table 1. Further, this invention covers the use of isolated or recombinant DNA, or fragments thereof, which encode proteins which are homologous to a CTLA-8 protein or which were isolated using cDNA encoding a CTLA-8 protein as a probe. The isolated DNA can have the respective regulatory sequences in the 5' and 3' flanks, e.g., promoters, enhancers, poly-A addition signals, and others. In particular, the murine CTLA-8 gene has significant homology, about 60%, to the putative protein encoded by the open reading frame ORF13, of herpesvirus Saimiri (Table 2); to a human CTLA-8 counterpart (Table 3), about 60%; and to a mouse CTLA-8 counterpart (Table 4), about 80%.

TABLE 2

Nucleotide sequence, SEQ ID NO.3, of the related herpesvirus Saimiri open reading frame ORF13 and predicted amino acid sequence of encoded protein, see GenBank/EMBL accession number M60286.

```
herpesvirus
AGCTTCATGC AAATACATCT TATCTTACCA GATTCTCGCC TCATTTGCAA    50

ACATGCCTCA TCTTTTGAGA AGAAACGCAA TTCGAACTTC TTCTAATGCT   100

CCTGAAGAGC AGCCTGTGCT GCAGCCTGAG CTTGATGCTA TTGAAGAGCT   150

AGAATAAGAG CTATTTTTTG ACGATGGGTG CTGCCTTTCT GTTCAAGAAA   200

TCTGCTTAAT TGTTCTTGGA TTCTTATTGT TTCTGCTAGC TGTAATTGTT   250

TTTTATAACT ATACAGACAC AGATCAATTT GTGAAGCTGA CACATCTTAT   300
```

TABLE 2-continued

Nucleotide sequence, SEQ ID NO.3, of the related herpesvirus Saimiri open reading frame ORF13 and predicted amino acid sequence of encoded protein, see GenBank/EMBL accession number M60286.

| Sequence | Position |
|---|---|
| GAGCCACAAA AATTCTATCA AAGGACCTTT TGATCTTTAA GGTATGTACT | 350 |
| CATAATTTTA TTTTTTTATT TCTAAAACAA TCTTAGTATA TATAATTAAT | 400 |
| ACAAATTTTA GAAAATACTA TAATAAATAT TGAAAGCTGT ATTTACATTG | 450 |
| TAAACTATAT ATAGGCAATG TAAAGTCATT CTAACTTTAG GTTTGCTTTA | 500 |
| CCTGTTACAG AAACTTCACC TGTGTGTCAA GAGCTGCAAA CATGGCTTTA | 550 |
| GACTTAAGAA ATCTTAAACA CCTGACTGCT AACTTCAGTT TTAGAATAAT | 600 |
| GATATGGATT ATGCTATGTT TGGCTCTACC TACTGATAGT AAACCTATTT | 650 |
| CAACAACTGA AGCTCCAATA CTAAACATAA CACAATCTCC AAGTTTGAAC | 700 |
| ATCTCATCAC CTTCTACTTT AGAACCTTCA GAGCCTCTTA AAAACTGTAC | 750 |
| AACATTCTTA GACTTACTTT GGCAGCGGCT GGGCGAGAAC GCTTCTATAA | 800 |
| AGGACTTGAT GTTAACATTA CAACGAGAAG AAGTCCACGG AAGAATGACT | 850 |
| ACACTTCCTT CACCTAGACC AAGCAGTAAA GTTGAAGAAC AACAGTTACA | 900 |
| AAGACCTAGA AACTTACTGC CTACTGCTGT CGGGCCACCT CATGTCAAAT | 950 |
| ATAGACTATA TAATCGCTTA TGGGAAGCTC CTAAAGGAGC TGATGTTAAT | 1000 |
| GGTAAACCTA TACAATTTGA TGACCCTCCT CTTCCTTATA CAGGGGCATA | 1050 |
| TAATGATGAT GGTGTTTTAA TGGTTAATAT TAATGGAAAA CATGTGAGGT | 1100 |
| TTGATAGCTT GTCTTATTGG GAAAGAATTA AAAGATCTGG TACCCCATGG | 1150 |
| TGTATAAAGA CACCAAGTGA AAAAGCAGCA ATATTGAAGC AGCTTTTAAA | 1200 |
| AGCTGAAAAA AAATGTAGGA CTACTTCTAA ACGTATCACT GAGTTAGAAG | 1250 |
| AGCAGATTAA AGAACTAGAA AAAACTAGTA CATCTCCATA GATTACTGTT | 1300 |
| AGAATGTGTT TATCATACTA AAATAAATGC TTTATGTATT GCAATATTAC | 1350 |
| TTGTTTGCTA TGACTTTGGT ATATGAAATG CAAATCTTAA ATAAAAAGTT | 1400 |
| TTTGTCTAGT ATTGGCGTCA CTGTATTTTA CTAGCAAAAA TATATAAATT | 1450 |
| GTTATGTAGC AAGAAGTTTG TATCAATATA AAAACTCTAA AGTATATAAA | 1500 |
| CAAACATTCA ATTAGTGTAA ATCATAGCAA GCATATCTTT TCATACGTGT | 1550 |
| CTAGTTAATT TAAAGAATTA ATTATGACAT TTAGAATGAC TTCACTTGTG | 1600 |
| TTACTTCTGC TGCTGAGCAT AGATTGTATA GTAAAGTCAG AAATAACAAG | 1650 |
| CGCACAAACC CCAAGATGCT TAGCTGCTAA CAATAGCTTT CCACGGTCTG | 1700 |
| TGATGGTTAC TTTGAGCATC CGTAACTGGA ATACTAGTTC TAAAAGGGCT | 1750 |
| TCAGACTACT ACAATAGATC TACGTCTCCT TGGACTCTCC ATCGCAATGA | 1800 |
| AGATCAAGAT AGATATCCCT CTGTGATTTG GAAGCAAAG TGTCGCTACT | 1850 |
| TAGGATGTGT TAATGCTGAT GGGAATGTAG ACTACCACAT GAACTCAGTC | 1900 |
| CCTATCCAAC AAGAGATTCT AGTGGTGCGC AAAGGGCATC AACCCTGCCC | 1950 |
| TAATTCATTT AGGCTAGAGA AGATGCTAGT GACTGTAGGC TGCACATGCG | 2000 |
| TTACTCCCAT TGTTCACAAT GTAGACTAAA AGCTATCTAA ATTTTGAAAA | 2050 |
| TTAACATTTC ACTAAAAAAC AAAAACTTGA TTTTTTTCTT TTAAATAAAA | 2100 |
| AAAGTTTAAT ATAAGTTCTG GCTTGTTTGG TTTTTGACTA ATCAATGTAG | 2150 |

TABLE 2-continued

Nucleotide sequence, SEQ ID NO.3, of the related herpesvirus Saimiri open reading frame ORF13 and predicted amino acid sequence of encoded protein, see GenBank/EMBL accession number M60286.

```
ATCACACTTG TGATCTTAGC TCTCGGGAAG CAATGTAAGA AAATATATTT    2200

AACTTAAGAG TTTTAGACTT GCTTGAGTTT TATGAGTAAA AAACAAAGAA    2250

TAAGCACAGC TTCTTGTATC TTCTTTTAAA AACTTTAAGT TATTTATGTA    2300

TTTAATATAA TCTAATGTTT CTTAAACATG TTGAGTTTGA GGTCCACTAA    2350

TACAACATTA TAATTTTTTC TGTTATAACA CTTTTGCAAG AAGAACTCAT    2400

TTTATAGAAA ATGAGCAGTA TTCAAAAAAA ATGTTTGATA TGCTGTAATA    2450

TTGGAGAGGA AGAACTTTTA CAAGCATGTG ATTGTCCTAG CAGAGTCCAT    2500

CATACATGCT TACAAAGTCA                                    2520
```

Tm17.Peptide sequence, SEQ ID NO.4
```
MVIDG CKKYM RRTCG DVLDN LRGDC YQVLI EDCIP VLKMY AKEGR EFDYV   50

INDLT AVPIS TSPEE DSTWD FLRLI LDLSM KVLKQ DGKTF TQGNC VNLTE  100

ALSLY EEQLG RLYCP VEFSK EIVCV PSYLE LWVFY TVWKK AKP          143
```

TABLE 3

Nucleotide sequence, SEQ ID NO.5, of human CTLA-8 fragment and predicted amino acid sequence, SEQ ID NO.6, of encoded protein.

```
AGC/CGC AAT GAG GAC CCT GAG AGA TAT CCC TCT GTG ATC TGG GAG
GCA AAG TGC CGC CAC TTG GGC TGC ATC AAC GCT GAT GGG AAC GTG
GAC TAC CAC ATG AAC TCT GTC CCC ATC CAG CAA GAG ATC CTG GTC
CTG CGC AGG GAG CCT CCA CAC TGC CCC AAC TCC TTC CGG CTG GAG
AAG ATA CTG GTG TCC GTG GGC TGC ACC TCT GTC ACC CCG ATT GTC
CAC CAT GTG GCC TAA
```

```
ser/arg asn glu asp pro glu arg tyr pro ser val ile trp glu
ala lys cys arg his leu gly cys ile asn ala asp gly asn val
asp tyr his met asn ser val pro ile gln gln glu ile leu val
leu arg arg glu pro pro his cys pro asn ser phe arg leu glu
lys ile leu val ser val gly cys thr cys val thr pro ile val
his his val ala OCH
``` this was used to isolate a full length clone from human; it corresponds to
nucleotides 272-510: SEQ ID NO.7 and 8

```
            GG CACAAACTCA TCCATCCCCA GTTGATTGGA      42
AGAAACAACG

ATG ACT CCT GGG AAG ACC TCA TTG GTG TCA CTG CTA       87
CTG CTG CTG
Met thr pro gly lys thr ser leu val ser leu leu       15
leu leu leu AGC CTG GAG GCC ATA GTG AAG GCA GGA ATC ACA ATC      132
CCA CGA AAT
ser leu glu ala ile val lys ala gly ile thr ile       30
pro arg asn CCA GGA TGC CCA AAT TCT GAG GAC AAG AAC TTC CCC      177
CGG ACT GTG
pro gly cys pro asn ser glu asp lys asn phe pro       45
arg thr val ATG GTC AAC CTG AAC ATC CAT AAC CGG AAT ACC AAT      222
ACC AAT CCC
met val asn leu asn ile his asn arg asb thr asn       60
thr asn pro
```

TABLE 3-continued

Nucleotide sequence, SEQ ID NO.5, of human CTLA-8 fragment and predicted amino acid sequence, SEQ ID NO.6, of encoded protein.

| | | | | | | | | | | |
|---|---|---|---|---|---|---|---|---|---|---|
| aaA | AGG | TCC | TCA | GAT | TAC | TAC | AAC | CGA | TCC | ACC TCA | 267 |
| CCT | TGG | AAT | | | | | | | | |
| lys | arg | ser | ser | asp | tyr | tyr | asn | arg | ser | thr ser | 75 |
| pro | trp | asn | | | | | | | | |
| CTC | CAC | CGC | AAT | GAG | GAC | CCT | GAG | AGA | TAT | CCC TCT | 312 |
| GTG | ATC | TGG | | | | | | | | |
| leu | his | arg | asn | glu | asp | pro | glu | arg | tyr | pro ser | 90 |
| val | ile | trp | | | | | | | | |
| GAG | GCA | AAG | TGC | CGC | CAC | TTG | GGC | TGC | ATC | AAC GCT | 357 |
| GAT | GGG | AAC | | | | | | | | |
| glu | ala | lys | cys | arg | his | leu | gly | cys | ile | asn ala | 105 |
| asp | gly | asn | | | | | | | | |
| GTG | GAC | TAC | CAC | ATG | AAC | TCT | GTC | CCC | ATC | CAG CAA | 402 |
| GAG | ATC | CTG | | | | | | | | |
| val | asp | tyr | his | met | asn | ser | val | pro | ile | gln gln | 120 |
| glu | ile | leu | | | | | | | | |
| GTC | CTG | CGC | AGG | GAG | CCT | CCA | CAC | TGC | CCC | AAC TCC | 447 |
| TTC | CGG | CTG | | | | | | | | |
| val | leu | arg | arg | glu | pro | pro | his | cys | pro | asn ser | 135 |
| phe | arg | leu | | | | | | | | |
| GAG | AAG | ATA | CTG | GTG | TCC | GTG | GGC | TGC | ACC | TGT GTC | 492 |
| ACC | CCG | ATT | | | | | | | | |
| glu | lys | ile | leu | val | ser | val | gly | cys | thr | cys val | 150 |
| thr | pro | ile | | | | | | | | |
| GTC | CAC | CAT | GTG | GCC | | | | | | | 510 |
| TAA | | | | | | | | | | | |
| val | his | his | val | ala | | | | | | | 156 |
| OCH | | | | | | | | | | | |

TABLE 4

Nucleotide sequences, SEQ ID NO.9, of mouse CTLA-8 fragment and predicted amino acid sequence of encoded protein.

| | |
|---|---|
| gaggctcaagtgcacccagcaccagctgatcaggacgcgcaaacatgagtccagggagagcttcatctg | 69 |
| tgtctctgatgctgttgctgctgctgagcctggcggctacagtgaaggcagcagcgatcatccctcaaa | 138 |
| gctcagcgtgtccaaacactgaggccaaggacttcctccagaatgtgaaggtcaacctcaaagtcttta | 207 |
| actcccTTGGCGCAAAAGTGAGCTCCAGAAGgCCCTCAGACTACCTCAACCGTTCCACGTCACCCTGGA | 276 |
| CTCTCCACCGCAATGAAGAcCCTGATAGATATCCCTCTGTGATCTGGGAAGCTCAGTGCCGCCACCAGC | 345 |
| GCTGTGTCAATGCGGAGggaaagctggaccaccacatgaattctgttctcatccagcaagagatcctgg | 414 |
| tcctgaagagggagcctgagagctgccccttcactttcagggtcgagaagatgctggtgggTGTGGGCT | 483 |
| GCACCTGCGTGGCCTCGATTGTCCGCCAGGCAGCCTAAACAGAGACCCGCGGCTGACCCCTAAGAAACC | 552 |
| CCCACGTTTCTCAGCAAACTTACTTGCATTTTTAAAACAGTTCGTGCTATTGATTTTCAGCAAGGAATG | 621 |
| TGGATTCAGAGGCAGATTCAGAATTGTCTGCCCTCCACAATGAAAAGAAGGTGTAAAGGGGTCCCAAAC | 690 |
| TGCTTCgtgtttgtttttctgtggactttaaattatttgtgtatttacaatatcccaagataactttga | 759 |
| aggcgtaacttatttaatgaagtatctacattattattatgtttctttctgaagaagacaaaattcaag | 828 |
| actcagaaattttattatttaaaaggtaagcctatatttatatgagctatttatgaatctatttatttt | 897 |
| tcttcagtatttgaagtattaagaacatgattttcAGATCTACCTAGGGAAGTCCTAAGTAAGATTAAA | 966 |
| TATTAATGGAAATTTCAGCTTTACTATTTGGTTGATTTAAGGTTCTCTCCTCTGAATGGGGTGAAAACC | 1035 |
| AAACTTAGTTTTATGTTTAATAACTTTTTAAATTATTGAAGATTCAAAAAATTGGATAATTTAGCTCCC | 1104 |
| TACTCTGTTTTAAAAAAAAAAAAAAAAAAA | 1134 |

TABLE 4-continued

Mouse CTLA-8 predicted amino acid sequence, SEQ ID NO.10. The mature polypeptide probably starts at a position about amino acid 19 (Leu) to amino acid 21 (Ala).

| | |
|---|---|
| METSerProGlyArgAlaSerSerValSerLeuMETLeuLeuLeuLeuLeuSerLeuAlaAlaThrValLys | 24 |
| AlaAlaAlaIleIleProGlnSerSerAlaCysProAsnThrGluAlaLysAspPheLeuGlnAsnValLys | 48 |
| ValAsnLeuLysValPheAsnSerLeuGlyAlaLysValSerSerArgArgProSerAspTyrLeuAsnArg | 72 |
| SerThrSerProTrpThrLeuHisArgAsnGluAspProAspArgTyrProSerValIleTrpGluAlaGln | 96 |
| CysArgHisGlnArgCysValAsnAlaGlyGlyLysLeuAspHisHisMETAsnSerValLeuIleGlnGln | 120 |
| GluIleLeuValLeuLysArgGluProGluSerCysProPheThrPheArgValGluLysMETLeuValGly | 144 |
| ValGlyCysThrCysValAlaSerIleValArgGlnAlaAla | 158 |

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. Alternatively, a purified species may be separated from host components from a recombinant expression system. The size of homology of such a nucleic acid will typically be less than large vectors, e.g., less than tens of kB, typically less than several kB, and preferably in the 2–6 kB range.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides. Said fragments may have termini at any location, but especially at boundaries between structural domains.

A DNA which codes for a CTLA-8 protein will be particularly useful to identify genes, mRNA, and cDNA species which code for related or homologous proteins, as well as DNAs which code for homologous proteins from different species. There are likely homologues in other species, including primates. Various CTLA-8 proteins should be homologous and are encompassed herein. However, even proteins that have a more distant evolutionary relationship to the antigen can readily be isolated under appropriate conditions using these sequences if they are sufficiently homologous. Primate CTLA-8 protein proteins are of particular interest.

This invention further covers recombinant DNA molecules and fragments having a DNA sequence identical to or highly homologous to the isolated DNAs set forth herein. In particular, the sequences will often be operably linked to DNA segments which control transcription, translation, and DNA replication. Alternatively, recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology* Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987)(ed.) *Teratocarcinomas and Embryonic Stem Cells: A Practical Approach* IRL Press, Oxford; Rosenberg (1992) *J. Clinical Oncology* 10:180–199; and Cournoyer and Caskey (1993) *Ann. Rev. Immunol.* 11:297–329.

Homologous nucleic acid sequences, when compared, exhibit significant similarity. The standards for homology in nucleic acids are either measures for homology generally used in the art by sequence comparison or based upon hybridization conditions. The hybridization conditions are described in greater detail below.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a sequence derived from Table 1, 2, or 3. Typically, selective hybridization will occur when there is at least about 55% homology over a stretch of at least about 14 nucleotides, preferably at least about 65%, more preferably at least about 75%, and most preferably at least about 90%. See, Kanehisa (1984) *Nuc. Acids Res.* 12:203–213. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) *J. Mol. Biol.* 31:349–370.

CTLA-8 protein from other mammalian species can be cloned and isolated by cross-species hybridization of closely related species, e.g., human, as disclosed in Table 3. Homology may be relatively low between distantly related species, and thus hybridization of relatively closely related species is advisable. Alternatively, preparation of an antibody preparation which exhibits less species specificity may be useful in expression cloning approaches.

III. Purified CTLA-8 Protein

The predicted sequence of murine CTLA-8 protein amino acid sequence is shown in Table 1. The homologous herpesvirus predicted ORF13 protein sequence is shown in Table 2, and is assigned SEQ ID NO: 4. A human counterpart is described in Table 3. The peptide sequences allow preparation of peptides to generate antibodies to recognize such segments.

As used herein, the terms "murine CTLA-8 protein" and "human CTLA-8 protein shall encompass, when used in a protein context, a protein having amino acid sequences shown in Table 1 or Table 3, or a significant fragment of such a protein. It also refers to a mouse derived polypeptide which exhibits similar biological function or interacts with CTLA-8 protein specific binding components. These binding components, e.g., antibodies, typically bind to a CTLA-8 protein with high affinity, e.g., at least about 100 nM, usually better than about 30 nM, preferably better than about 10 nM, and more preferably at better than about 3 nM. Homologous proteins would be found in mammalian species other than rat or humans, e.g., mouse, primates, and in the herpesvirus genome, e.g., ORF13. Non-mammalian species should also possess structurally or functionally related genes and proteins.

The term "polypeptide" as used herein includes a significant fragment or segment, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. The specific ends of such a segment will be at any combinations within the protein, preferably encompassing structural domains.

The term "binding composition" refers to molecules that bind with specificity to CTLA-8 protein, e.g., in a ligand-receptor type fashion, an antibody-antigen interaction, or compounds, e.g., proteins which specifically associate with CTLA-8 protein, e.g., in a natural physiologically relevant protein-protein interaction, either covalent or non-covalent. The molecule may be a polymer, or chemical reagent. No implication as to whether CTLA-8 protein is either the ligand or the receptor of a ligand-receptor interaction is represented, other than the interaction exhibit similar specificity, e.g., specific affinity. A functional analog may be a protein with structural modifications, or may be a wholly unrelated molecule, e.g., which has a molecular shape which interacts with the appropriate binding determinants. The proteins may serve as agonists or antagonists of a receptor, see, e.g., Goodman, et al. (eds.) (1990) *Goodman & Gilman's: The Pharmacological Bases of Therapeutics* (8th ed.), Pergamon Press.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified, e.g., to conform to standard buffers used in physiological or analytical contexts.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS or CHAPS, or a low enough concentration as to avoid significant disruption of structural or physiological properties of the antigen.

Solubility is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W. H. Freeman; and Cantor and Schimmel (1980) *Biophysical Chemistry*, parts 1–3, W. H. Freeman & Co., San Francisco. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30 S, more typically less than about 15 S, usually less than about 10 S, more usually less than about 6 S, and, in particular embodiments, preferably less than about 4 S, and more preferably less than about 3 S.

IV. Making CTLA-8 Protein; Mimetics

DNA which encodes the CTLA-8 protein or fragments thereof can be obtained by chemical synthesis, screening CDNA libraries, or by screening genomic libraries prepared from a wide variety of cell lines or tissue samples.

This DNA can be expressed in a wide variety of host cells for the synthesis of a full-length protein or fragments which can in turn, for example, be used to generate polyclonal or monoclonal antibodies; for binding studies; for construction and expression of modified molecules; and for structure/function studies. Each antigen or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, or portions thereof, may be expressed as fusions with other proteins.

Expression vectors are typically self-replicating DNA or RNA constructs containing the desired antigen gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell. Methods for amplifying vector copy number are also known, see, e.g., Kaufman, et al. (1985) *Molec. and Cell. Biol.* 5:1750–1759.

The vectors of this invention contain DNA which encodes a CTLA-8 protein, or a fragment thereof, typically encoding a biologically active polypeptide. The DNA can be under the control of a viral promoter and can encode a selection marker. This invention further contemplates use of such expression vectors which are capable of expressing eukaryotic cDNA coding for a CTLA-8 protein in a prokaryotic or eukaryotic host, where the vector is compatible with the host and where the eukaryotic cDNA coding for the antigen is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the antigen or its fragments in various hosts using vectors that do not contain a replication origin that is recognized by the host cell. It is also possible to use vectors that cause integration of a CTLA-8 protein gene or its fragments into the host DNA by recombination, or to integrate a promoter which controls expression of an endogenous gene.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual,* Elsevier, N.Y., and Rodriquez, et al. (1988)(eds.) *Vectors: A Survey of Molecular Cloning Vectors and Their Uses,* Buttersworth, Boston, Mass.

Transformed cells include cells, preferably mammalian, that have been transformed or transfected with vectors containing a CTLA-8 gene, typically constructed using recombinant DNA techniques. Transformed host cells usually express the antigen or its fragments, but for purposes of cloning, amplifying, and manipulating its DNA, do not need to express the protein. This invention further contemplates culturing transformed cells in a nutrient medium, thus permitting the protein to accumulate in the culture. The protein can be recovered, either from the culture or from the culture medium.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis.* Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the CTLA-8 proteins or its fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses,* Buttersworth, Boston, Chapter 10, pp. 205–236.

Lower eukaryotes, e.g., yeasts and Dictyostelium, may be transformed with vectors encoding CTLA-8 proteins. For purposes of this invention, the most common lower eukaryotic host is the baker's yeast, Saccharomyces cerevisiae. It will be used to generically represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the functionally active CTLA-8 protein. In principle, many higher eukaryotic tissue culture cell lines are workable, e.g., insect baculovirus expression systems, whether from an invertebrate or vertebrate source. However, mammalian cells are preferred, in that the processing, both cotranslationally and posttranslationally. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610, see O'Reilly, et al. (1992) *Baculovirus Exoression Vectors: A Laboratory Manual* Freeman and Co., CRC Press, Boca Raton, Fla.

It will often be desired to express a CTLA-8 protein polypeptide in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the CTLA-8 protein gene may be co-transformed with one or more genes encoding mammalian or other glycosylating enzymes. Using this approach, certain mammalian glycosylation patterns will be achievable or approximated in prokaryote or other cells.

The CTLA-8 protein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283.

Now that the CTLA-8 protein has been characterized, fragments or derivatives thereof can be prepared by conventional processes for synthesizing peptides. These include processes such as are described in Stewart and Young (1984) *Solid Phase Peptide Synthesis,* Pierce Chemical Co., Rockford, Ill.; Bodanszky and Bodanszky (1984) *The Practice of Peptide Synthesis,* Springer-Verlag, New York; and Bodanszky (1984) *The Principles of Peptide Synthesis,* Springer-Verlag, New York. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The CTLA-8 protein, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction are typically protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonyl-hydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. (1963) in *J. Am. Chem. Soc.* 85:2149–2156.

The prepared protein and fragments thereof can be isolated and purified from the reaction mixture by means of peptide separation, for example, by extraction, precipitation, electrophoresis and various forms of chromatography, and the like. The CTLA-8 proteins of this invention can be obtained in varying degrees of purity depending upon its desired use. Purification can be accomplished by use of the protein purification techniques disclosed herein or by the use of the antibodies herein described in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the protein, or lysates or supernatants of cells producing the CTLA-8 protein as a result of DNA techniques, see below.

V. Physical Variants

This invention also encompasses proteins or peptides having substantial amino acid sequence homology with the amino acid sequence of the CTLA-8 protein. The variants include species or allelic variants.

Amino acid sequence homology, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural allelic and interspecies variations in each respective protein sequence. Typical homologous proteins or peptides will have from 25–100% homology (if gaps can be introduced), to 50–100% homology (if conservative substitutions are included) with the amino acid sequence of the CTLA-8 protein. Homology measures will be at least about 35%, generally at least 40%, more generally at least 45%, often at least 50%, more often at least 55%, typically at least 60%, more typically at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443–453; Sankoff, et al. (1983) Chapter One in *Time Warps, String Edits, and Macromolecules: The Theory and Practice of Sequence Comparison* Addison-Wesley, Reading, Mass.; and software packages from IntelliGenetics, Mountain View, Calif.; and the University of Wisconsin Genetics Computer Group, Madison, Wis.

The isolated DNA encoding a CTLA-8 protein can be readily modified by nucleotide substitutions, nucleotide deletions, nucleotide insertions, and inversions of nucleotide stretches. These modifications result in novel DNA sequences which encode these antigens, their derivatives, or proteins having similar physiological, immunogenic, or antigenic activity. These modified sequences can be used to produce mutant antigens or to enhance expression. Enhanced expression may involve gene amplification, increased transcription, increased translation, and other mechanisms. Such mutant CTLA-8 protein derivatives include predetermined or site-specific mutations of the respective protein or its fragments. "Mutant CTLA-8 protein" encompasses a polypeptide otherwise falling within the homology definition of the murine CTLA-8 or human CTLA-8 protein as set forth above, but having an amino acid sequence which differs from that of CTLA-8 protein as found in nature, whether by way of deletion, substitution, or insertion. In particular, "site specific mutant CTLA-8 protein" generally includes proteins having significant homology with a protein having sequences of Table 1, 2, or 3, and as sharing various biological activities, e.g., antigenic or immunogenic, with those sequences, and in preferred embodiments contain most of the disclosed sequences. Similar concepts apply to different CTLA-8 proteins, particularly those found in various warm blooded animals, e.g., mammals and birds. As stated before, it is emphasized that descriptions are generally meant to encompass all CTLA-8 proteins, not limited to the mouse embodiment specifically discussed.

Although site specific mutation sites are predetermined, mutants need not be site specific. CTLA-8 protein mutagenesis can be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also Sambrook, et al. (1989) and Ausubel, et al. (1987 and Supplements).

The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with a CTLA-8 polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, antigen-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992. Thus, new chimeric polypeptides exhibiting new combinations of specificities will result from the functional linkage of biologically relevant domains and other functional domains.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

VI. Functional Variants

The blocking of physiological response to CTLA-8 proteins may result from the inhibition of binding of the antigen to its natural binding partner, e.g., through competitive inhibition. Thus, in vitro assays of the present invention will often use isolated protein, membranes from cells expressing a recombinant membrane associated CTLA-8 protein, soluble fragments comprising binding segments, or fragments attached to solid phase substrates. These assays will also allow for the diagnostic determination of the effects of either binding segment mutations and modifications, or protein mutations and modifications, e.g., analogs.

This invention also contemplates the use of competitive drug screening assays, e.g., where neutralizing antibodies to antigen or binding partner fragments compete with a test compound for binding to the protein. In this manner, the antibodies can be used to detect the presence of any polypeptide which shares one or more antigenic binding sites of the protein and can also be used to occupy binding sites on the protein that might otherwise interact with a binding partner.

Additionally, neutralizing antibodies against the CTLA-8 protein and soluble fragments of the antigen which contain a high affinity receptor binding site, can be used to inhibit antigen function in tissues, e.g., tissues experiencing abnormal physiology.

"Derivatives" of the CTLA-8 antigens include amino acid sequence mutants, glycosylation variants, and covalent or aggregate conjugates with other chemical moieties. Covalent derivatives can be prepared by linkage of functionalities to groups which are found in the CTLA-8 amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the CTLA-8 protein or fragments thereof with other proteins or polypeptides. These derivatives can be synthesized in recombinant culture such as N- or C-terminal fusions or by the use of agents known in the art for their usefulness in cross-linking proteins through reactive side groups. Preferred antigen derivatization sites with cross-linking agents are at free amino groups, carbohydrate moieties, and cysteine residues.

Fusion polypeptides between the CTLA-8 proteins and other homologous or heterologous proteins are also provided. Homologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of an antigen, e.g., a receptor-binding segment, so that the presence or location of the fused antigen may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, for example, in Sambrook, et al. (1989) *Molecular Cloning: A Laboratory Manual* (2d ed.), Vols. 1–3, Cold Spring Harbor Laboratory. Techniques for synthesis of polypeptides are described, for example, in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach,* IRL Press, Oxford.

This invention also contemplates the use of derivatives of the CTLA-8 proteins other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of antigens or other binding proteins. For example, a CTLA-8 antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-CTLA-8 protein antibodies or its receptor or other binding partner. The CTLA-8 antigens can also be labeled with a detectable group, for example radioiodinated by the chloramine T procedure, covalently bound to rare earth chelates, or conjugated to another fluorescent moiety for use in diagnostic assays. Purification of CTLA-8 protein may be effected by immobilized antibodies or binding partners.

A solubilized CTLA-8 antigen or fragment of this invention can be used as an immunogen for the production of antisera or antibodies specific for the protein or fragments thereof. The purified antigen can be used to screen monoclonal antibodies or binding fragments prepared by immunization with various forms of impure preparations containing the protein. In particular, the term "antibodies" also encompasses antigen binding fragments of natural antibodies. The purified CTLA-8 proteins can also be used as a reagent to detect any antibodies generated in response to the presence of elevated levels of the protein or cell fragments containing the antigen, both of which may be diagnostic of an abnormal or specific physiological or disease condition. Additionally, antigen fragments may also serve as immunogens to produce the antibodies of the present invention, as described immediately below. For example, this invention contemplates antibodies raised against amino acid sequences encoded by nucleotide sequences shown in Table 1, 2, or 3, or fragments of proteins containing them. In particular, this invention contemplates antibodies having binding affinity to or being raised against specific fragments which are predicted to lie outside of the lipid bilayer.

The present invention contemplates the isolation of additional closely related species variants. Southern blot analysis established that similar genetic entities exist in other mammals, e.g., rat and human. It is likely that the CTLA-8 proteins are widespread in species variants, e.g., rodents, lagomorphs, carnivores, artiodactyla, perissodactyla, and primates.

The invention also provides means to isolate a group of related antigens displaying both distinctness and similarities in structure, expression, and function. Elucidation of many of the physiological effects of the antigens will be greatly accelerated by the isolation and characterization of distinct species variants. In particular, the present invention provides useful probes for identifying additional homologous genetic entities in different species.

The isolated genes will allow transformation of cells lacking expression of a corresponding CTLA-8 protein, e.g., either species types or cells which lack corresponding antigens and should exhibit negative background activity. Expression of transformed genes will allow isolation of antigenically pure cell lines, with defined or single specie variants. This approach will allow for more sensitive detection and discrimination of the physiological effects of CTLA-8 proteins. Subcellular fragments, e.g., cytoplasts or membrane fragments, can be isolated and used.

Dissection of the critical structural elements which effect the various physiological or differentiation functions provided by the proteins is possible using standard techniques of modern molecular biology, particularly in comparing members of the related class. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390.

In particular, functional domains or segments can be substituted between species variants to determine what structural features are important in both binding partner affinity and specificity, as well as signal transduction. An array of different variants will be used to screen for molecules exhibiting combined properties of interaction with different species variants of binding partners.

Antigen internalization may occur under certain circumstances, and interaction between intracellular components and "extracellular" segments of proteins involved in interactions may occur. The specific segments of interaction of CTLA-8 protein with other intracellular components may be identified by mutagenesis or direct biochemical means, e.g., cross-linking or affinity methods. Structural analysis by crystallographic or other physical methods will also be applicable. Further investigation of the mechanism of biological function will include study of associated components which may be isolatable by affinity methods or by genetic means, e.g., complementation analysis of mutants.

Further study of the expression and control of CTLA-8 protein will be pursued. The controlling elements associated with the antigens may exhibit differential developmental, tissue specific, or other expression patterns. Upstream or downstream genetic regions, e.g., control elements, are of interest.

Structural studies of the antigen will lead to design of new variants, particularly analogs exhibiting agonist or antagonist properties on binding partners. This can be combined with previously described screening methods to isolate variants exhibiting desired spectra of activities.

Expression in other cell types will often result in glycosylation differences in a particular antigen. Various species variants may exhibit distinct functions based upon structural differences other than amino acid sequence. Differential modifications may be responsible for differential function, and elucidation of the effects are now made possible.

Thus, the present invention provides important reagents related to antigen-binding partner interaction. Although the foregoing description has focused primarily upon the murine CTLA-8 and human CTLA-8 protein, those of skill in the art will immediately recognize that the invention encompasses other antigens, e.g., mouse and other mammalian species or allelic variants, as well as variants thereof.

VII. Antibodies

Antibodies can be raised to the various CTLA-8 proteins, including species or allelic variants, and fragments thereof, both in their naturally occurring forms and in their recombinant forms. Additionally, antibodies can be raised to CTLA-8 proteins in either their active forms or in their inactive forms. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective CTLA-8 proteins, or screened for agonistic or antagonistic activity, e.g., mediated through a binding partner. These monoclonal antibodies will usually bind with at least a $K_D$ of about 1 mM, more usually at least about 300 $\mu$M, typically at least about 10 $\mu$M, more typically at least about 30 $\mu$M, preferably at least about 10 $\mu$M, and more preferably at least about 3 $\mu$M or better.

The antibodies, including antigen binding fragments, of this invention can have significant diagnostic or therapeutic value. They can be potent antagonists that bind to a binding partner and inhibit antigen binding or inhibit the ability of an antigen to elicit a biological response. They also can be useful as non-neutralizing antibodies and can be coupled to toxins or radionuclides so that when the antibody binds to the antigen, a cell expressing it, e.g., on its surface, is killed. Further, these antibodies can be conjugated to drugs or other therapeutic agents, either directly or indirectly by means of a linker, and may effect drug targeting.

The antibodies of this invention can also be useful in diagnostic applications. As capture or non-neutralizing antibodies, they can be screened for ability to bind to the antigens without inhibiting binding by a partner. As neutralizing antibodies, they can be useful in competitive binding assays. They will also be useful in detecting or quantifying CTLA-8 protein or its binding partners. See, e.g., Chan (ed.) (1987) *Immunoassay: A Practical Guide* Academic Press, Orlando, Fla.; Ngo (ed.) (1988) *Nonisotopic Immunoassay* Plenum Press, N.Y.; and Price and Newman (eds.) (1991) *Principles and Practice of Immunoassay* Stockton Press, NY.

Antigen fragments may be joined to other materials, particularly polypeptides, as fused or covalently joined polypeptides to be used as immunogens. An antigen and its fragments may be fused or covalently linked to a variety of immunogens, such as keyhole limpet hemocyanin, bovine serum albumin, tetanus toxoid, etc. See *Microbiology,* Hoeber Medical Division, Harper and Row, 1969; Landsteiner (1962) *Specificity of Serological Reactions,* Dover Publications, New York, and Williams, et al. (1967) *Methods in Immunology and Immunochemistry,* Vol. 1, Academic Press, New York, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual,* CSH Press; Goding (1986) *Monoclonal Antibodies: Principles and Practice* (2d ed.) Academic Press, New York; and particularly in Kohler and Milstein (1975) in *Nature* 256: 495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567.

The antibodies of this invention can also be used for affinity chromatography in isolating the protein. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified CTLA-8 protein will be released.

The antibodies may also be used to screen expression libraries for particular expression products. Usually the antibodies used in such a procedure will be labeled with a moiety allowing easy detection of presence of antigen by antibody binding.

Antibodies raised against each CTLA-8 protein will also be useful to raise anti-idiotypic antibodies. These will be useful in detecting or diagnosing various immunological conditions related to expression of the respective antigens.

VIII. Uses

The present invention provides reagents which will find use in diagnostic applications as described elsewhere herein, e.g., in the general description for physiological or developmental abnormalities, or below in the description of kits for diagnosis.

This invention also provides reagents with significant therapeutic value. The CTLA-8 protein (naturally occurring or recombinant), fragments thereof, and antibodies thereto, along with compounds identified as having binding affinity to CTLA-8 protein, should be useful in the treatment of conditions associated with abnormal physiology or development, including abnormal proliferation, e.g., cancerous conditions, or degenerative conditions. Abnormal proliferation, regeneration, degeneration, and atrophy may be modulated by appropriate therapeutic treatment using the compositions provided herein. For example, a disease or disorder associated with abnormal expression or abnormal signaling by a CTLA-8 antigen should be a likely target for an agonist or antagonist of the protein.

Other abnormal developmental conditions are known in the cell types shown to possess CTLA-8 antigen mRNA by Northern blot analysis. See Berkow (ed.) *The Merck Manual of Diagnosis and Therapy,* Merck & Co., Rahway, N.J.; and Thorn, et al. *Harrison's Principles of Internal Medicine,* McGraw-Hill, N.Y. These problems may be susceptible to prevention or treatment using compositions provided herein.

Recombinant antibodies which bind to CTLA-8 can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Screening using CTLA-8 for binding partners or compounds having binding affinity to CTLA-8 antigen can be performed, including isolation of associated components. Subsequent biological assays can then be utilized to determine if the compound has intrinsic biological activity and is therefore an agonist or antagonist in that it blocks an activity of the antigen. This invention further contemplates the therapeutic use of antibodies to CTLA-8 protein as antagonists. This approach should be particularly useful with other CTLA-8 protein species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa. Methods for administration are discussed therein and below, e.g., for oral, intravenous, intraperitoneal, or intramuscular administration, transdermal diffusion, and others. See also Langer (1990) *Science* 249:1527–1533. Pharmaceutically acceptable carriers will include water, saline, buffers, and other compounds described, e.g., in the *Merck Index,* Merck & Co., Rahway, N.J. Dosage ranges would ordinarily be expected to be in amounts lower than 1 mM concentrations, typically less than about 10 µM concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

CTLA-8 protein, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics,* 8th Ed., Pergamon Press, Parrytown, N.Y.; *Remington's Pharmaceutical Sciences,* 17th ed. (1990), Mack Publishing Co., Easton, Pa.; Avis, et al. (eds.) (1993) *Pharmaceutical Dosage Forms: Parenteral Medications* 2d ed., Dekker, N.Y.; Lieberman, et al. (eds.) (1990) *Pharmaceutical Dosage Forms: Tablets* 2d ed., Dekker, N.Y.; and Lieberman, et al. (eds.) (1990) *Pharmaceutical Dosage Forms: Disperse Systems* Dekker, N.Y. The therapy of this invention may be combined with or used in association with other chemotherapeutic or chemopreventive agents.

Both the naturally occurring and the recombinant forms of the CTLA-8 proteins of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, which describes means for testing of binding affinity by a plurality of defined polymers synthesized on a solid substrate. The development of suitable assays can be greatly facilitated by the availability of large amounts of purified, soluble CTLA-8 protein as provided by this invention.

This invention is particularly useful for screening compounds by using recombinant antigen in any of a variety of drug screening techniques. The advantages of using a recombinant protein in screening for specific ligands include: (a) improved renewable source of the antigen from a specific source; (b) potentially greater number of antigen molecules per cell giving better signal to noise ratio in assays; and (c) species variant specificity (theoretically giving greater biological and disease specificity). The purified protein may be tested in numerous assays, typically in vitro assays, which evaluate biologically relevant responses. See, e.g., Coligan *Current Protocols in Immunology;* Hood, et al. *Immunology* Benjamin/Cummings; Paul (ed.) *Fundamental Immunology;* and *Methods in Enzymology* Academic Press.

One method of drug screening utilizes eukaryotic or prokaryotic host cells which are stably transformed with recombinant DNA molecules expressing the CTLA-8 antigens. Cells may be isolated which express an antigen in isolation from other functionally equivalent antigens. Such cells, either in viable or fixed form, can be used for standard protein-protein binding assays. See also, Parce, et al. (1989) *Science* 246:243–247; and Owicki, et al. (1990) *Proc. Nat'l Acad. Sci. USA* 87:4007–4011, which describe sensitive methods to detect cellular responses. Competitive assays are particularly useful, where the cells (source of CTLA-8 protein) are contacted and incubated with a labeled binding partner or antibody having known binding affinity to the ligand, such as $^{125}$I-antibody, and a test sample whose binding affinity to the binding composition is being measured. The bound and free labeled binding compositions are then separated to assess the degree of antigen binding. The amount of test compound bound is inversely proportional to the amount of labeled receptor binding to the known source. Any one of numerous techniques can be used to separate bound from free antigen to assess the degree of binding. This separation step could typically involve a procedure such as adhesion to filters followed by washing, adhesion to plastic followed by washing, or centrifugation of the cell membranes. Viable cells could also be used to screen for the effects of drugs on CTLA-8 protein mediated functions, e.g., second messenger levels, i.e., $Ca^{++}$; cell proliferation; inositol phosphate pool changes; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Another method utilizes membranes from transformed eukaryotic or prokaryotic host cells as the source of the CTLA-8 protein. These cells are stably transformed with DNA vectors directing the expression of a membrane associated CTLA-8 protein, e.g., an engineered membrane bound form. Essentially, the membranes would be prepared from the cells and used in any receptor/ligand type binding assay such as the competitive assay set forth above.

Still another approach is to use solubilized, unpurified or solubilized, purified CTLA-8 protein from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to CTLA-8 and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified CTLA-8 binding composition, and washed. The next step involves detecting bound binding composition.

Rational drug design may also be based upon structural studies of the molecular shapes of the CTLA-8 protein and other effectors or analogs. Effectors may be other proteins which mediate other functions in response to antigen binding, or other proteins which normally interact with the antigen. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York.

Purified CTLA-8 protein can be coated directly onto plates for use in the aforementioned drug screening techniques. However, non-neutralizing antibodies to these ligands can be used as capture antibodies to immobilize the respective ligand on the solid phase.

IX. Kits

This invention also contemplates use of CTLA-8 proteins, fragments thereof, peptides, and their fusion products in a variety of diagnostic kits and methods for detecting the presence of a binding composition. Typically the kit will have a compartment containing either a defined CTLA-8 peptide or gene segment or a reagent which recognizes one or the other, e.g., antigen fragments or antibodies.

A kit for determining the binding affinity of a test compound to a CTLA-8 protein would typically comprise a test compound; a labeled compound, for example an antibody having known binding affinity for the antigen; a source of CTLA-8 protein (naturally occurring or recombinant); and a means for separating bound from free labeled compound, such as a solid phase for immobilizing the antigen. Once compounds are screened, those having suitable binding affinity to the antigen can be evaluated in suitable biological assays, as are well known in the art, to determine whether they exhibit similar biological activities to the natural antigen. The availability of recombinant CTLA-8 protein polypeptides also provide well defined standards for calibrating such assays.

A preferred kit for determining the concentration of, for example, a CTLA-8 protein in a sample would typically comprise a labeled compound, e.g., antibody, having known binding affinity for the antigen, a source of antigen (naturally occurring or recombinant) and a means for separating the bound from free labeled compound, for example, a solid phase for immobilizing the CTLA-8 protein. Compartments containing reagents, and instructions, will normally be provided.

One method for determining the concentration of CTLA-8 protein in a sample would typically comprise the steps of: (1) preparing membranes from a sample comprised of a membrane bound CTLA-8 protein source; (2) washing the membranes and suspending them in a buffer; (3) solubilizing the antigen by incubating the membranes in a culture medium to which a suitable detergent has been added; (4) adjusting the detergent concentration of the solubilized antigen; (5) contacting and incubating said dilution with radiolabeled antibody to form complexes; (6) recovering the complexes such as by filtration through polyethyleneimine treated filters; and (7) measuring the radioactivity of the recovered complexes.

Antibodies, including antigen binding fragments, specific for the CTLA-8 protein or fragments are useful in diagnostic applications to detect the presence of elevated levels of CTLA-8 protein and/or its fragments. Such diagnostic assays can employ lysates, live cells, fixed cells, immunofluorescence, cell cultures, body fluids, and further can involve the detection of antigens related to the protein in serum, or the like. Diagnostic assays may be homogeneous (without a separation step between free reagent and protein-protein complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to a CTLA-8 protein or to a particular fragment thereof. Similar assays have also been extensively discussed in the literature. See, e.g., Harlow and Lane (1988) *Antibodies: A Laboratory Manual*, CSH.

Anti-idiotypic antibodies may have similar use to diagnose presence of antibodies against a CTLA-8 protein, as such may be diagnostic of various abnormal states. For example, overproduction of CTLA-8 protein may result in production of various immunological reactions which may be diagnostic of abnormal physiological states, particularly in proliferative cell conditions such as cancer or abnormal differentiation.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled CTLA-8 protein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the antigen, test compound, CTLA-8 protein, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free antigen, or alternatively the bound from the free test compound. The CTLA-8 protein can be immobilized on various matrixes followed by washing. Suitable matrixes include plastic such as an ELISA plate, filters, and beads. Methods of immobilizing the CTLA-8 protein to a matrix include, without limitation, direct adhesion to plastic, use of a capture antibody, chemical coupling, and biotin-avidin. The last step in this approach involves the precipitation of protein-protein complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

The methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a CTLA-8 protein. These sequences can be used as probes for detecting levels of antigen message in samples from patients suspected of having an abnormal condition, e.g., cancer or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}P$. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

The broad scope of this invention is best understood with reference to the following examples, which are not intended to limit the invention to specific embodiments.

EXAMPLES

I. General Methods

Some of the standard methods are described or referenced, e.g., in Maniatis, et al. (1982) *Molecular Cloning, A Laboratory Manual,* Cold Spring Harbor Laboratory, Cold Spring Harbor Press; Sambrook, et al. (1989) *Molecular Cloning: A Laboratory Manual,* (2d ed.), vols. 1–3, CSH Press, NY; Ausubel, et al., *Biology,* Greene Publishing Associates, Brooklyn, N.Y.; or Ausubel, et al. (1987 and Supplements) *Current Protocols in Molecular Biology,* Greene/Wiley, New York; Innis, et al. (eds.) (1990) *PCR Protocols: A Guide to Methods and Applications* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology,* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *QIAexpress: The High Level Expression & Protein Purification System* QUIAGEN, Inc., Chatsworth, Calif.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Isolation of a DNA Clone Encoding CTLA-8 Protein

Isolation of murine CTLA-8 is described in Rouvier, et al. (1993) *J. Immunol.* 150:5445–5456.

Source of the CTLA-8 Message

Various cell lines are screened using an appropriate probe for high level message expression. Appropriate cell lines are selected based upon expression levels of the CTLA-8 message. Applicants used subtractive hybridization methods on activated cytotoxic T cells.

Isolation of a CTLA-8 Encoding Clone

Standard PCR techniques are used to amplify a CTLA-8 gene sequence from a genomic or cDNA library, or from mRNA. Appropriate primers are selected from the sequences provided, and a full length clone is isolated. Various combinations of primers, of various lengths and possibly with differences in sequence, may be prepared. The full length clone can be used as a hybridization probe to screen for other homologous genes using stringent or less stringent hybridization conditions.

In another method, oligonucleotides are used to screen a library. In combination with polymerase chain reaction (PCR) techniques, synthetic oligonucleotides in appropriate orientations are used as primers to select correct clones from a library.

III. Isolation of a Human CTLA-8.

A human genomic library was obtained from Clontech (Cat. HL1006d) and screened with a cDNA probe composed of a 453 base pair entire coding sequence of a murine CTLA-8. A number of independent lambda clones were found to hybridize strongly with the murine CTLA-8 probe. One clone contained a hybridizing XbaI fragment of approximately 2000 base pairs which corresponded to a fragment previously detected using a similar probe on a human genomic DNA Southern blot. This 2000 base pair fragment was subcloned into Bluescript (Stratagene) and sequenced. This revealed a 240 base pair region (see Table 3) 83.8% homologous to the murine CTLA-8 of Table 1. Translation of this region yielded an amino acid sequence 70.8% homologous to the 79 carboxy-terminal amino acids of the murine CTLA-8 putative protein. The exon was used as a probe to screen a library of cDNA made with a primer corresponding to the last 21 nucleotides of the coding region. Three independent cDNA clones were obtained containing the complete coding region of the human CTLA-8. The 468 base pair open reading frame encodes a 155 amino acid polypeptide with a theoretical molecular weight of 17,100 daltons. See Table 3. This human CTLA-8 is 66.4% homologous to the ORF-13 of the virus, and 58.3% homologous to murine CTLA-8 encoded protein. Moreover, the 6 cysteines are conserved between the three genes, as well as the putative glycosylation and phosphorylation sites.

Analysis of the human CTLA-8 amino acid sequence exhibits a hydrophobic stretch of 19 residues, from 7 to about 25, at the amino terminus, similar to a signal peptide. It is highly likely that the human CTLA-8 is a secreted protein of a molecular weight resembling a cytokine.

IV. Biochemical Characterization of CTLA-8 Proteins

Two forms of human CTLA-8 were expressed in heterologous cells; the native form, and a recombinant form displaying the FLAG peptide at the carboxy terminus. See, e.g., Crowe et al. (1992) *OIAexpress: The High Level Expression and Protein Purification System* QIAGEN, Inc. Chatsworth, Calif.; and Hopp et al. (1988) *Bio/Technology* 6:1204–1210. These two forms of the human CTLA-8 protein were introduced into the expression vectors pME18S or pEE12, and subsequently transfected into COS-7 or NSO cells, respectively, by electroporation. Electroporated cells were then cultivated for 48 hours in RPMI medium supplemented with 10% Fetal Calf Serum. Cells were then incubated with $^{35}$S-Met and $^{35}$S-Cys in order to label cellular proteins. Comparison of the proteins under reducing conditions on SDS-PAGE showed that cells transfected with human CTLA-8 secreted a polypeptide of 15,000 daltons. Non-reducing SDS-PAGE revealed 2 specific bands around 28,000 daltons and 33,000 daltons. Treatment with endoglycosidase F (Boehringer Mannheim) demonstrated that the higher molecular weight species represents an N-glycosylated form of human CTLA-8.

In order to determine if the natural form of human CTLA-8 produced by activated CD4+ T cells was also secreted as a dimer similar to transfected COS-7 and NSO cells, peripheral blood mononuclear cells (PBMC) were purified from 500 ml of human blood on a Ficoll gradient. B cells, CD8+ T cells, monocytes, and NK cells were depleted using 100 μl of ascitic fluid containing anti-CD19, anti-CD8, anti-CD14, and 25 μg of NKH1 monoclonal antibody (Coulter, Hialeah, Fla.). After 30 minutes of incubation at 4° C., the PBMC were washed twice in RPMI containing 10% Fetal Calf Serum (FCS). Paramagnetic beads coated with goat antibodies to mouse IgG (Dynabeads M450, Dynal, Oslo, Norway) were added at a final concentration of 5 beads/cell to be depleted. Unwanted cells were subsequently removed by 3 passages on a magnet. The remaining cells were CD4+ cells at 87% purity which were diluted to $10^7$ cells/ml in DMEM F12 (Gibco, Gaithersburg, Md.) containing 10% FCS, 10 ng/ml PMA (Sigma, St. Louis, Mo.) and 500 ng/ml ionomycin (Sigma, St. Louis, Mo.). After incubation for 4 hours at 37° C. in 5% $CO_2$, the medium was changed to methionine and cysteine free DMEM (ICN Biomedicals, Costa Mesa, Calif.), supplemented with 1% dialyzed FCS, 10 ng/ml PMA and 500 ng/ml ionomycin, and incubated for 1 hour at 37° C. in 5% $CO_2$. 100 μCi/ml of 35S-methionine and 35S-cysteine (Amersham) was added, and metabolic labeling was carried out for 18 hours at 37° C. in 5% $CO_2$. Following preclearing of the supernatants with anti-IFN-γ Mab B27 and 0.5 ml of Protein-G Sepharose (Sigma St. Louis, Mo.), the supernatants were immunoprecipated using monoclonal antibodies to human CTLA-8. Immunoprecipated proteins were analyzed on SDS-PAGE. CD4+ T cells and transfected NSO cells reveal two bands at 28,000 and 33,000 daltons corresponding respectively to non N-glycosylated and N-glycosylated forms of human CTLA-8 dimers. Therefore, human CTLA-8 derived from transfected NSO cells and CTLA-8 isolated from activated T cells display the same biological characteristics.

V. Large Scale Production of Human CTLA-8

For biological assays, human CTLA-8 and human CTLA-8-FLAG were produced in large amounts with transfected COS-7 cells grown in RPMI medium supplemented with 1% Nutridoma HU (Boeringer Mannheim, Mannheim, Germany) and subsequently purified.

In order to produce larger quantities of native human CTLA-8 or human CTLA-8-FLAG, stable transformants of NSO cells were prepared according to the methodology developed by Celltech (Slough, Berkshire, UK; International Patent Applications WO86/05807, WO87/04462, WO89/01036, and WO89/10404). Both CTLA-8 and CTLA-8-FLAG were subcloned into pEE12 and subsequently transfected into NSO cells by electroporation. Transfected NSO cells were seeded in selective glutamine-free DMEM supplemented with 10% Fetal Calf Serum as described in Celltech's protocol. Supernatants from the best producing lines were used in biological assays and purification of human CTLA-8 and human CTLA-8-FLAG.

Purification of Human CTLA-8 Protein

Typically, 1 liter of supernatant containing human CTLA-8 or CTLA-8-FLAG was passed on a 60 ml column of $Zn^{++}$ ions grafted to a Chelating Sepharose Fast Flow matrix (Pharmacia, Upsalla, Sweden). After washing with 10 volumes of binding buffer (His-Bind Buffer kit, Novagen, Madison, Wis.), the proteins retained by the metal ions were eluted with a gradient of 20–100 mM Imidazole. The content of human CTLA-8-FLAG in the eluted fractions was determined by dot blot using the anti-FLAG monoclonal antibody M2 (Eastman Kodak, New Haven, Conn.), whereas the content of human CTLA-8 was assessed by silver staining of non-reducing SDS-PAGE. The CTLA-8 containing fractions were then pooled and dialyzed against PBS, and were either used in biological assays or further purified by anion exchange HPLC on a DEAE column. A third step of gle filtration chromatograph was performed on a SUPERDEX G-75 HRD30 column (Pharmacia Uppsala, Sweden) and yielded practically pure human CTLA-8-8 as analyzed by silver stained SDS-PAGE.

Preparation of Antibodies Specific for CTLA-8

Inbred Balb/c mice were immunized intraperitoneally with 1 ml of purified human CTLA-8-FLAG emulsified in Freund's complete adjuvant on day 0, and in Freund's incomplete adjuvant on days 15 and 22. The mice were boosted with 0.5 ml of purified human CTLA-8-8 administered intravenously.

Hybridomas were created using the non-secreting myeloma cells line SP2/0-Ag8 and polyethylene glycol 1000 (Sigma, St. Louis, Mo.) as the fusing agent. Hybridoma cells were placed in a 96-well Falcon tissue culture plate (Becton Dickinson, New Jersey) and fed with DMEM F12 (Gibco, Gaithersburg, Md.) supplemented with 80 μg/ml gentamycin, 2 mM glutamine, 10% horse serum (Gibco, Gaithersburg, Md.), 1% ADCM (CRTS, Lyon, France) $10^{-5}$ M azaserine (Sigma, St. Louis, Mo.) and $5 \times 10^{-5}$ M hypoxanthine. Hybridoma supernatants were screened for antibody production against human CTLA-8 by immunocytochemistry (ICC) using acetone fixed human CTLA-8 transfected COS-7 cells and by ELISA using human CTLA-8-FLAG purified from COS-7 supernatants as a coating antigen. Aliquots of positive cell clones were expanded for 6 days and cryopreserved as well as propagated in ascites from pristane (2,6,10,14-teramethylpentadecane, Sigma, St. Louis, Mo.) treated Balb/c mice who had received on intraperitoneal injection of pristane 15 days before. About $10^5$ hybridoma cells in 1 ml of PBS were given intraperitoneally, and 10 days later, ascites were collected from each mouse.

After centrifugation of the ascites, the antibody fraction was isolated by ammonium sulfate precipitation and anion-exchange chromatography on a zephyr-D silicium column (IBF Sepracor) equilabrated with 20 mM Tris pH 8.0. Proteins were eluted with a NaCl gradient (ranging from 0 to 1 M NaCl). 2 ml fractions were collected and tested by ELISA for the presence of anti-CTLA-8 antibody. The fractions containing specific anti-CTLA-8 activity were pooled, dialyzed, and frozen. Aliquots of the purified monoclonal antibodies were peroxydase labeled.

Quantification of Human CTLA-8

Among the antibodies specific for CTLA-8, Ab25, and peroxydase labeled Ab16 were selected to quantitate levels of human CTLA-8 using a sandwich assay. Purified Ab25 was diluted at 2 µg/ml in coating buffer (carbonate buffer, pH 9.6. 15 mM $Na_2CO_3$, 35 mM $NaHCO_3$). This diluted solution was coated onto the wells of a 96-well ELISA plate (Immunoplate Maxisorp F96 certified, NUNC, Denmark) overnight at room temperature. The plates were then washed manually one with a washing buffer consisting of Phosphate Buffered Saline and 0.05% Tween 20 (Technicon Diagnositics, USA). 110 µl of purified human CTLA-8 diluted in TBS-B-T buffer [20 mM Tris, 150 mM NaCl, 1% BSA (Sigma, St. Louis, Mo.), and 0.05% Tween 20] was added to each well. After 3 hours of incubation at 37° C., the plates were washed once. 100 µl of peroxydase labeled Ab16 diluted to 5 µg/ml in TBS-B-T buffer was added to each well, and incubated for 2 hours at 37° C. The wells were then washed three times in washing buffer. 100 µl of peroxydase substrate, 2.2'Azino-bis(3 ethylbenzthiazoine-6-sulfonic acid) (ABTS), diluted to 1 mg/ml in citrate/phosphate buffer, was added to each well, and the colorimetric reaction was read at 405 nm. The lowest concentration of human CTLA-8 detected was 0.015 ng/ml.

V. Induction of IL-6 Secretion by Treatment of Various Cell Types with CTLA-8

Synoviocytes from normal and rheumatoid arthritic patients ($10^4$ cells/well) were incubated with increasing concentrations of human CTLA-8-8. After 48 hours, concentrations of IL-6 were measured by standard ELISA techniques. Secretion of IL-6 was increased in both types of cells in a dose dependent manner.

Kidney epithelial carcinoma cell lines TUMT and CHA were also cultured in complete RPMI 1640 medium (Gibco BRL, Grand Island, N.Y.), supplemented with 2 mM L-glutamine, 100 U/ml penicillin, 50 µg/ml gentamycin, 20 mM Hepes buffer and heat-inactivated 10% FCS. Cells ($10^4$ cells/well) were incubated in 96-well plates (Falcon) in a final volume of 250 µl of complete culture medium. Increasing concentrations of human CTLA-8-8 were added at the onset of the culture. Cell-free supernatants were collected after 48 hours, and stored at −20° C. until cytokine assays. IL-6 levels were measured by two-site sandwich ELISA as described in Abrams, et al. (1992). *Immunol. Rev.* 127:5–24. Both cell lines exhibited dose dependent increases in IL-6 secretion with increasing concentrations of CTLA-8. In view of these results, other cell lines will also be screened for responses to other species of CTLA-8 variants.

MRC-5 human lung fibroblasts were obtained from the ATCC (Rockville, Md.) and were cultured in complete RPMI 1640 medium (Gibco BRL, Grand Island, N.Y.), supplemented with 2mM L-glutamine, 100 U/ml penicillin, 50 mg/ml gentamycin, 20 mM Hepes buffer and heat-inactivated 10% FCS. Cells ($10^4$ cells/well) were incubated in 96-well plates (Falcon) in a final volume of 250 ml of complete culture medium. Increasing concentrations of human CTLA-8-8 was added at the onset of the culture. Cell-free supernatants were collected after 48 hours, and stored at −20° C. until cytokine assays. IL-6 levels, measured by ELISA. Dose dependent induction of IL-6 was observed.

Similar results were obtained using adult and child dermal fibroblasts, human brain epithelial cells, and human bronchus epithelial cells. Kidney mesangium cells are also expected to respond similarly.

VI. Isolating CTLA-8 Homologues

The binding composition is used for screening of an expression library made from a cell line which expresses a CTLA-8 protein. Standard staining techniques are used to detect or sort intracellular or surface expressed antigen, or surface expressing transformed cells are screened by panning. Screening of intracellular expression is performed by various staining or immunofluorescence procedures. See also McMahan, et al. (1991) *EMBO J.* 10:2821–2832.

For example, on day 0, precoat 2-chamber permanox slides with 1 ml per chamber of fibronectin, 10 ng/ml in PBS, for 30 min at room temperature. Rinse once with PBS. Then plate COS cells at 2–3×$10^5$ cells per chamber in 1.5 ml of growth media. Incubate overnight at 37° C.

On day 1 for each sample, prepare 0.5 ml of a solution of 66 µg/ml DEAE-dextran, 66 µM chloroquine, and 4 µg DNA in serum free DME. For each set, a positive control is prepared, e.g., of huIL-10-FLAC cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin (0.1%) with 32 µl/ml of 1 M $NaN_3$ for 20 min. Cells are then washed with HBSS/saponin 1×. Soluble antibody is added to cells and incubate for 30 min. Wash cells twice with HBSS/saponin. Add second antibody, e.g., Vector anti-mouse antibody, at 1/200 dilution, and incubate for 30 min. Prepare ELISA solution, e.g., Vector Elite ABC horseradish peroxidase solution, and pre-incubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. wash cells twice with HBSS, second wash for 2 min, which closes cells. Then add Vector diaminobenzoic acid (DAB) for 5 to 10 min. Use 2 drops of buffer plus 4 drops DAB plus 2 drops of $H_2O_2$ per 5 ml of glass distilled water. Carefully remove chamber and rinse slide in water. Air dry for a few minutes, then add 1 drop of Crystal Mount and a cover slip. Bake for 5 min at 85–90° C.

Alternatively, the binding compositions are used to affinity purify or sort out cells expressing the antigen. See, e.g., Sambrook, et al. or Ausubel, et al.

Similar methods are applicable to isolate either species or allelic variants. Species variants are isolated using cross-species hybridization techniques based upon a full length isolate or fragment from one species as a probe, or appropriate species.

All references cited herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An antibody which specifically binds a mammalian CTLA-8 protein or peptide thereof, wherein said antibody blocks a CTLA-8 induced secretion of an inflammatory mediator.

2. The antibody of claim 1, wherein said antibody is raised against a peptide sequence of SEQ ID NO: 2, 4, 6, or 8.

3. The antibody of claim 2, wherein said antibody is a monoclonal antibody.

4. The antibody of claim 3, wherein said inflammatory mediator is selected from the group consisting of IL6, IL-8 and PGE2.

5. An antibody of claim 3, wherein said antibody is labeled.

6. A kit comprising a substantially pure CTLA-8 protein and an antibody specific to a mammalian CTLA-8, wherein said antibody blocks a CTLA-8 induced secretion of an inflammatory mediator.

7. An antibody reactive with a human CTLA-8 said antibody raised against a peptide of SEQ ID NO: 8, wherein said antibody blocks a CTLA-8 induced secretion of an inflammatory mediator.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1080 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 12..464

(xi) SEQUENCE DESCRIPTION: SEQ ID NO:1:

```
GAATTCCATC C ATG TGC CTG ATG CTG TTG CTG CTA CTG AAC CTG GAG GCT      50
            Met Cys Leu Met Leu Leu Leu Leu Leu Asn Leu Glu Ala
             1               5                  10

ACA GTG AAG GCA GCG GTA CTC ATC CCT CAA AGT TCA GTG TGT CCA AAC       98
Thr Val Lys Ala Ala Val Leu Ile Pro Gln Ser Ser Val Cys Pro Asn
 15              20                  25

GCC GAG GCC AAT AAC TTT CTC CAG AAC GTG AAG GTC AAC CTG AAA GTC      146
Ala Glu Ala Asn Asn Phe Leu Gln Asn Val Lys Val Asn Leu Lys Val
 30              35                  40                  45

ATC AAC TCC CTT AGC TCA AAA GCG AGC TCC AGA AGG CCC TCA GAC TAC      194
Ile Asn Ser Leu Ser Ser Lys Ala Ser Ser Arg Arg Pro Ser Asp Tyr
                 50                  55                  60

CTC AAC CGT TCC ACT TCA CCC TGG ACT CTG AGC CGC AAT GAG GAC CCT      242
Leu Asn Arg Ser Thr Ser Pro Trp Thr Leu Ser Arg Asn Glu Asp Pro
             65                  70                  75

GAT AGA TAT CCT TCT GTG ATC TGG GAG GCA CAG TGC CGC CAC CAG CGC      290
Asp Arg Tyr Pro Ser Val Ile Trp Glu Ala Gln Cys Arg His Gln Arg
         80                  85                  90

TGT GTC AAC GCT GAG GGG AAG TTG GAC CAC CAC ATG AAT TCT GTT CTC      338
Cys Val Asn Ala Glu Gly Lys Leu Asp His His Met Asn Ser Val Leu
     95                 100                 105

ATC CAG CAA GAG ATC CTG GTC CTG AAG AGG GAG CCT GAG AAG TGC CCC      386
Ile Gln Gln Glu Ile Leu Val Leu Lys Arg Glu Pro Glu Lys Cys Pro
110             115                 120                 125

TTC ACT TTC CGG GTG GAG AAG ATG CTG GTG GGC GTG GGC TGC ACC TGC      434
Phe Thr Phe Arg Val Glu Lys Met Leu Val Gly Val Gly Cys Thr Cys
                130                 135                 140

GTT TCC TCT ATT GTC CGC CAT GCG TCC TAA ACAGAGACCT GAGGCTAGCC        484
Val Ser Ser Ile Val Arg His Ala Ser  *
                145                 150

CCTAAGAAAC CCCTGCGTTT CTCTGCAAAC TTCCTTGTCT TTTTAAAACA GTTCACAGTT    544

GAATCTCAGC AAGTGATATG GATTTAAAGG CGGGGTTAGA ATTGTCTGCC TTCCACCCTG    604

AAAAGAAGGC GCAGAGGGGA TATAAATTGC TTCTTGTTTT TCTGTGGGCT TTAAATTATT    664

TATGTATTTA CTCTATCCCG AGATAACTTT GAGGCATAAG TTATTTTAAT GAATTATCTA    724

CATTATTATT ATGTTTCTTA ATGCAGAAGA CAAAATTCAA GACTAAGAAA TTTTATTATT    784

TAAAAGGTAA AACCTATATT TATATGAGCT ATTTATGGGT CTATTTATTT TCTTCAGTG    844

CTAAGATCAT GATTATCAGA TCTACCTAAG GAAGTCCTAA ATAATATTAA ATATTAATTG    904

AAATTTCAGT TTTACTATTT GCTTATTTAA GGTTCCCTCC TCTGAATGGT GTGAAATCAA    964
```

```
ACCTCGTTTT ATGTTTTTAA ATTATTGAGG CTTCGAAAAA TTGGGCAATT TAGCTTCCTA    1024

CTGTGTGTTT AAAAACCTTG TAACAATATC ACTATAATAA ATTTTTGGAA GAAAAT        1080
```

(2) INFORMATION FOR SEQ ID NO:2:

(i) SEQUENCE CHARACTERISTICS:
        (A) LENGTH: 150 amino acids
        (B) TYPE: amino acid
        (D) TOPOLOGY: linear (ii) MOLECULE TYPE: protein (xi) SEQUENCE DESCRIPTION: SEQ ID NO:2:

```
Met Cys Leu Met Leu Leu Leu Leu Asn Leu Glu Ala Thr Val Lys
 1               5                  10                  15

Ala Ala Val Leu Ile Pro Gln Ser Ser Val Cys Pro Asn Ala Glu Ala
                20                  25                  30

Asn Asn Phe Leu Gln Asn Val Lys Val Asn Leu Lys Val Ile Asn Ser
                35                  40                  45

Leu Ser Ser Lys Ala Ser Ser Arg Arg Pro Ser Asp Tyr Leu Asn Arg
        50                  55                  60

Ser Thr Ser Pro Trp Thr Leu Ser Arg Asn Glu Asp Pro Asp Arg Tyr
65                  70                  75                  80

Pro Ser Val Ile Trp Glu Ala Gln Cys Arg His Gln Arg Cys Val Asn
                85                  90                  95

Ala Glu Gly Lys Leu Asp His His Met Asn Ser Val Leu Ile Gln Gln
                100                 105                 110

Glu Ile Leu Val Leu Lys Arg Glu Pro Glu Lys Cys Pro Phe Thr Phe
            115                 120                 125

Arg Val Glu Lys Met Leu Val Gly Val Gly Cys Thr Cys Val Ser Ser
        130                 135                 140

Ile Val Arg His Ala Ser
145             150
```

(2) INFORMATION FOR SEQ ID NO:3:

(i) SEQUENCE CHARACTERISTICS:
        (A) LENGTH: 456 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..453

(xi) SEQUENCE DESCRIPTION: SEQ ID NO:3:

```
ATG ACA TTT AGA ATG ACT TCA CTT GTG TTA CTT CTG CTG CTG AGC ATA     48
Met Thr Phe Arg Met Thr Ser Leu Val Leu Leu Leu Leu Leu Ser Ile
 1               5                  10                  15

GAT TGT ATA GTA AAG TCA GAA ATA ACA AGC GCA CAA ACC CCA AGA TGC     96
Asp Cys Ile Val Lys Ser Glu Ile Thr Ser Ala Gln Thr Pro Arg Cys
                20                  25                  30

TTA GCT GCT AAC AAT AGC TTT CCA CGG TCT GTG ATG GTT ACT TTG AGC    144
Leu Ala Ala Asn Asn Ser Phe Pro Arg Ser Val Met Val Thr Leu Ser
            35                  40                  45

ATC CGT AAC TGG AAT ACT AGT TCT AAA AGG GCT TCA GAC TAC TAC AAT    192
Ile Arg Asn Trp Asn Thr Ser Ser Lys Arg Ala Ser Asp Tyr Tyr Asn
        50                  55                  60
```

```
AGA TCT ACG TCT CCT TGG ACT CTC CAT CGC AAT GAA GAT CAA GAT AGA      240
Arg Ser Thr Ser Pro Trp Thr Leu His Arg Asn Glu Asp Gln Asp Arg
 65              70                  75                  80

TAT CCC TCT GTG ATT TGG GAA GCA AAG TGT CGC TAC TTA GGA TGT GTT      288
Tyr Pro Ser Val Ile Trp Glu Ala Lys Cys Arg Tyr Leu Gly Cys Val
                 85                  90                  95

AAT GCT GAT GGG AAT GTA GAC TAC CAC ATG AAC TCA GTC CCT ATC CAA      336
Asn Ala Asp Gly Asn Val Asp Tyr His Met Asn Ser Val Pro Ile Gln
            100                 105                 110

CAA GAG ATT CTA GTG GTG CGC AAA GGG CAT CAA CCC TGC CCT AAT TCA      384
Gln Glu Ile Leu Val Val Arg Lys Gly His Gln Pro Cys Pro Asn Ser
        115                 120                 125

TTT AGG CTA GAG AAG ATG CTA GTG ACT GTA GGC TGC ACA TGC GTT ACT      432
Phe Arg Leu Glu Lys Met Leu Val Thr Val Gly Cys Thr Cys Val Thr
130                 135                 140

CCC ATT GTT CAC AAT GTA GAC TAA                                      456
Pro Ile Val His Asn Val Asp
145                 150

(2) INFORMATION FOR SEQ ID NO:4:

(i) SEQUENCE CHARACTERISTICS:
        (A) LENGTH: 151 amino acids
        (B) TYPE: amino acid
        (D) TOPOLOGY: linear (ii) MOLECULE TYPE: protein (xi) SEQUENCE DESCRIPTION: SEQ ID NO:4:

Met Thr Phe Arg Met Thr Ser Leu Val Leu Leu Leu Leu Ser Ile
  1               5                  10                  15

Asp Cys Ile Val Lys Ser Glu Ile Thr Ser Ala Gln Thr Pro Arg Cys
                 20                  25                  30

Leu Ala Ala Asn Asn Ser Phe Pro Arg Ser Val Met Val Thr Leu Ser
            35                  40                  45

Ile Arg Asn Trp Asn Thr Ser Ser Lys Arg Ala Ser Asp Tyr Tyr Asn
        50                  55                  60

Arg Ser Thr Ser Pro Trp Thr Leu His Arg Asn Glu Asp Gln Asp Arg
 65              70                  75                  80

Tyr Pro Ser Val Ile Trp Glu Ala Lys Cys Arg Tyr Leu Gly Cys Val
                 85                  90                  95

Asn Ala Asp Gly Asn Val Asp Tyr His Met Asn Ser Val Pro Ile Gln
            100                 105                 110

Gln Glu Ile Leu Val Val Arg Lys Gly His Gln Pro Cys Pro Asn Ser
        115                 120                 125

Phe Arg Leu Glu Lys Met Leu Val Thr Val Gly Cys Thr Cys Val Thr
130                 135                 140

Pro Ile Val His Asn Val Asp
145                 150

(2) INFORMATION FOR SEQ ID NO:5:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: cDNA (ix) FEATURE:
```

(A) NAME/KEY: CDS
            (B) LOCATION: 1..240

(xi) SEQUENCE DESCRIPTION: SEQ ID NO:5:

AGC CGC AAT GAG GAC CCT GAG AGA TAT CCC TCT GTG ATC TGG GAG GCA       48
Ser Arg Asn Glu Asp Pro Glu Arg Tyr Pro Ser Val Ile Trp Glu Ala
 1               5                  10                  15

AAG TGC CGC CAC TTG GGC TGC ATC AAC GCT GAT GGG AAC GTG GAC TAC       96
Lys Cys Arg His Leu Gly Cys Ile Asn Ala Asp Gly Asn Val Asp Tyr
                20                  25                  30

CAC ATG AAC TCT GTC CCC ATC CAG CAA GAG ATC CTG GTC CTG CGC AGG      144
His Met Asn Ser Val Pro Ile Gln Gln Glu Ile Leu Val Leu Arg Arg
            35                  40                  45

GAG CCT CCA CAC TGC CCC AAC TCC TTC CGG CTG GAG AAG ATA CTG GTG      192
Glu Pro Pro His Cys Pro Asn Ser Phe Arg Leu Glu Lys Ile Leu Val
        50                  55                  60

TCC GTG GGC TGC ACC TGT GTC ACC CCG ATT GTC CAC CAT GTG GCC TAA      240
Ser Val Gly Cys Thr Cys Val Thr Pro Ile Val His His Val Ala *
65                  70                  75                  80

(2) INFORMATION FOR SEQ ID NO:6:

(i) SEQUENCE CHARACTERISTICS:
        (A) LENGTH: 79 amino acids
        (B) TYPE: amino acid
        (D) TOPOLOGY: linear (ii) MOLECULE TYPE: protein (xi) SEQUENCE DESCRIPTION: SEQ ID NO:6:

Ser Arg Asn Glu Asp Pro Glu Arg Tyr Pro Ser Val Ile Trp Glu Ala
 1               5                  10                  15

Lys Cys Arg His Leu Gly Cys Ile Asn Ala Asp Gly Asn Val Asp Tyr
                20                  25                  30

His Met Asn Ser Val Pro Ile Gln Gln Glu Ile Leu Val Leu Arg Arg
            35                  40                  45

Glu Pro Pro His Cys Pro Asn Ser Phe Arg Leu Glu Lys Ile Leu Val
        50                  55                  60

Ser Val Gly Cys Thr Cys Val Thr Pro Ile Val His His Val Ala
65                  70                  75                  80

(2) INFORMATION FOR SEQ ID NO:7:

(i) SEQUENCE CHARACTERISTICS:
        (A) LENGTH: 510 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 43..507

(xi) SEQUENCE DESCRIPTION: SEQ ID NO:7:

GGCACAAACT CATCCATCCC CAGTTGATTG GAAGAAACAA CG ATG ACT CCT GGG        54
                                              Met Thr Pro Gly
                                                1

AAG ACC TCA TTG GTG TCA CTG CTA CTG CTG CTG AGC CTG GAG GCC ATA      102
Lys Thr Ser Leu Val Ser Leu Leu Leu Leu Leu Ser Leu Glu Ala Ile
  5                  10                  15                  20

GTG AAG GCA GGA ATC ACA ATC CCA CGA AAT CCA GGA TGC CCA AAT TCT      150
Val Lys Ala Gly Ile Thr Ile Pro Arg Asn Pro Gly Cys Pro Asn Ser

```
                       25                  30                  35
GAG GAC AAG AAC TTC CCC CGG ACT GTG ATG GTC AAC CTG AAC ATC CAT       198
Glu Asp Lys Asn Phe Pro Arg Thr Val Met Val Asn Leu Asn Ile His
                40                  45                  50

AAC CGG AAT ACC AAT ACC AAT CCC AAA AGG TCC TCA GAT TAC TAC AAC       246
Asn Arg Asn Thr Asn Thr Asn Pro Lys Arg Ser Ser Asp Tyr Tyr Asn
            55                  60                  65

CGA TCC ACC TCA CCT TGG AAT CTC CAC CGC AAT GAG GAC CCT GAG AGA       294
Arg Ser Thr Ser Pro Trp Asn Leu His Arg Asn Glu Asp Pro Glu Arg
        70                  75                  80

TAT CCC TCT GTG ATC TGG GAG GCA AAG TGC CGC CAC TTG GGC TGC ATC       342
Tyr Pro Ser Val Ile Trp Glu Ala Lys Cys Arg His Leu Gly Cys Ile
85                  90                  95                 100

AAC GCT GAT GGG AAC GTG GAC TAC CAC ATG AAC TCT GTC CCC ATC CAG       390
Asn Ala Asp Gly Asn Val Asp Tyr His Met Asn Ser Val Pro Ile Gln
                105                 110                 115

CAA GAG ATC CTG GTC CTG CGC AGG GAG CCT CCA CAC TGC CCC AAC TCC       438
Gln Glu Ile Leu Val Leu Arg Arg Glu Pro Pro His Cys Pro Asn Ser
            120                 125                 130

TTC CGG CTG GAG AAG ATA CTG GTG TCC GTG GGC TGC ACC TGT GTC ACC       486
Phe Arg Leu Glu Lys Ile Leu Val Ser Val Gly Cys Thr Cys Val Thr
        135                 140                 145

CCG ATT GTC CAC CAT GTG GCC TAA                                       510
Pro Ile Val His His Val Ala
    150                 155

(2) INFORMATION FOR SEQ ID NO:8:

(i) SEQUENCE CHARACTERISTICS:
        (A) LENGTH: 155 amino acids
        (B) TYPE: amino acid
        (D) TOPOLOGY: linear (ii) MOLECULE TYPE: protein (xi) SEQUENCE DESCRIPTION: SEQ ID NO:8:

Met Thr Pro Gly Lys Thr Ser Leu Val Ser Leu Leu Leu Leu Ser
 1               5                  10                  15

Leu Glu Ala Ile Val Lys Ala Gly Ile Thr Ile Pro Arg Asn Pro Gly
                20                  25                  30

Cys Pro Asn Ser Glu Asp Lys Asn Phe Pro Arg Thr Val Met Val Asn
            35                  40                  45

Leu Asn Ile His Asn Arg Asn Thr Asn Thr Asn Pro Lys Arg Ser Ser
        50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

(2) INFORMATION FOR SEQ ID NO:9:
```

```
(i) SEQUENCE CHARISTICS:
    (A) LENGTH: 1134 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 45..521

(xi) SEQUENCE DESCRIPTION: SEQ ID NO:9:

GAGGCTCAAG TGCACCCAGC ACCAGCTGAT CAGGACGCGC AAAC ATG AGT CCA GGG    56
                                                Met Ser Pro Gly
                                                 1

AGA GCT TCA TCT GTG TCT CTG ATG CTG TTG CTG CTG CTG AGC CTG GCG    104
Arg Ala Ser Ser Val Ser Leu Met Leu Leu Leu Leu Leu Ser Leu Ala
 5               10                  15                      20

GCT ACA GTG AAG GCA GCA GCG ATC ATC CCT CAA AGC TCA GCG TGT CCA    152
Ala Thr Val Lys Ala Ala Ala Ile Ile Pro Gln Ser Ser Ala Cys Pro
                 25                  30                      35

AAC ACT GAG GCC AAG GAC TTC CTC CAG AAT GTG AAG GTC AAC CTC AAA    200
Asn Thr Glu Ala Lys Asp Phe Leu Gln Asn Val Lys Val Asn Leu Lys
             40                  45                      50

GTC TTT AAC TCC CTT GGC GCA AAA GTG AGC TCC AGA AGG CCC TCA GAC    248
Val Phe Asn Ser Leu Gly Ala Lys Val Ser Ser Arg Arg Pro Ser Asp
         55                  60                      65

TAC CTC AAC CGT TCC ACG TCA CCC TGG ACT CTC CAC CGC AAT GAA GAC    296
Tyr Leu Asn Arg Ser Thr Ser Pro Trp Thr Leu His Arg Asn Glu Asp
     70                  75                      80

CCT GAT AGA TAT CCC TCT GTG ATC TGG GAA GCT CAG TGC CGC CAC CAG    344
Pro Asp Arg Tyr Pro Ser Val Ile Trp Glu Ala Gln Cys Arg His Gln
 85                  90                      95                 100

CGC TGT GTC AAT GCG GAG GGA AAG CTG GAC CAC CAC ATG AAT TCT GTT    392
Arg Cys Val Asn Ala Glu Gly Lys Leu Asp His His Met Asn Ser Val
                105                 110                     115

CTC ATC CAG CAA GAG ATC CTG GTC CTG AAG AGG GAG CCT GAG AGC TGC    440
Leu Ile Gln Gln Glu Ile Leu Val Leu Lys Arg Glu Pro Glu Ser Cys
            120                 125                     130

CCC TTC ACT TTC AGG GTC GAG AAG ATG CTG GTG GGT GTG GGC TGC ACC    488
Pro Phe Thr Phe Arg Val Glu Lys Met Leu Val Gly Val Gly Cys Thr
        135                 140                     145

TGC GTG GCC TCG ATT GTC CGC CAG GCA GCC TAA ACAGAGACCC GCGGCTGACC  541
Cys Val Ala Ser Ile Val Arg Gln Ala Ala  *
    150                 155

CCTAAGAAAC CCCCACGTTT CTCAGCAAAC TTACTTGCAT TTTTAAAACA GTTCGTGCTA    601

TTGATTTTCA GCAAGGAATG TGGATTCAGA GGCAGATTCA GAATTGTCTG CCCTCCACAA    661

TGAAAAGAAG GTGTAAAGGG GTCCCAAACT GCTTCGTGTT TGTTTTCTG TGGACTTTAA    721

ATTATTTGTG TATTTACAAT ATCCCAAGAT AACTTTGAAG GCGTAACTTA TTTAATGAAG    781

TATCTACATT ATTATTATGT TTCTTTCTGA AGAAGACAAA ATTCAAGACT CAGAAATTTT    841

ATTATTTAAA AGGTAAGCCT ATATTTATAT GAGCTATTTA TGAATCTATT TATTTTTCTT    901

CAGTATTTGA AGTATTAAGA ACATGATTTT CAGATCTACC TAGGGAAGTC CTAAGTAAGA    961

TTAAATATTA ATGGAAATTT CAGCTTTACT ATTTGGTTGA TTTAAGGTTC TCTCCTCTGA   1021

ATGGGGTGAA AACCAAACTT AGTTTTATGT TTAATAACTT TTTAAATTAT TGAAGATTCA   1081

AAAAATTGGA TAATTTAGCT CCCTACTCTG TTTTAAAAAA AAAAAAAAA AAA           1134
```

-continued (2) INFORMATION FOR SEQ ID NO:10:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ser Pro Gly Arg Ala Ser Ser Val Ser Leu Met Leu Leu Leu Leu
 1               5                  10                  15

Leu Ser Leu Ala Ala Thr Val Lys Ala Ala Ile Ile Pro Gln Ser
            20                  25                  30

Ser Ala Cys Pro Asn Thr Glu Ala Lys Asp Phe Leu Gln Asn Val Lys
        35                  40                  45

Val Asn Leu Lys Val Phe Asn Ser Leu Gly Ala Lys Val Ser Ser Arg
    50                  55                  60

Arg Pro Ser Asp Tyr Leu Asn Arg Ser Thr Ser Pro Trp Thr Leu His
65                  70                  75                  80

Arg Asn Glu Asp Pro Asp Arg Tyr Pro Ser Val Ile Trp Glu Ala Gln
                85                  90                  95

Cys Arg His Gln Arg Cys Val Asn Ala Glu Gly Lys Leu Asp His His
            100                 105                 110

Met Asn Ser Val Leu Ile Gln Gln Glu Ile Leu Val Leu Lys Arg Glu
        115                 120                 125

Pro Glu Ser Cys Pro Phe Thr Phe Arg Val Glu Lys Met Leu Val Gly
    130                 135                 140

Val Gly Cys Thr Cys Val Ala Ser Ile Val Arg Gln Ala Ala
145                 150                 155
```